United States Patent
Cassells (12)

(10) Patent No.: US 6,730,521 B1
(45) Date of Patent: May 4, 2004

(54) CHEMICAL AND BIOCHEMICAL ASSAY METHOD AND APPARATUS

(75) Inventor: John Cassells, Cambs (GB)

(73) Assignee: The Technology Partnership PLC (GB)

( * ) Notice: Subject to any disclaimer, the term of this patent is extended or adjusted under 35 U.S.C. 154(b) by 0 days.

(21) Appl. No.: 09/913,630

(22) PCT Filed: Feb. 16, 2000

(86) PCT No.: PCT/GB00/00549

§ 371 (c)(1),
(2), (4) Date: Aug. 16, 2001

(87) PCT Pub. No.: WO00/49415

PCT Pub. Date: Aug. 24, 2000

(30) Foreign Application Priority Data

Feb. 16, 1999 (GB) .............................................. 9903555

(51) Int. Cl.[7] .............................................. G01N 33/53
(52) U.S. Cl. .................. 436/523; 436/151; 436/100; 436/800; 436/806; 435/174; 435/176; 435/240.2; 435/240.25; 435/288.3
(58) Field of Search ................................ 435/174, 176, 435/240.2, 240.23, 240.25, 288.1, 288.3; 436/523, 151, 100, 800, 806

(56) References Cited

U.S. PATENT DOCUMENTS 5,663,057 A * 9/1997 Drocourt et al. ........... 435/40.5
5,837,551 A * 11/1998 Ekins ......................... 436/518

OTHER PUBLICATIONS

Stuart Blincko and Raymond Edwards Non–separation assay for glycohemoglobin 44 (1998) 1302–1308.*

* cited by examiner

Primary Examiner—Long V. Le
Assistant Examiner—Jacob Cheu
(74) Attorney, Agent, or Firm—Cantor Colburn LLP

(57) ABSTRACT

A chemical and bio-chemical assay method is described which screens compounds for enzyme inhibition, or receptor or other target binding. Inhibition or binding by the library compounds causes a change in the amount of an optically detectable label that is bound to suspendable cells or solid supports. The amounts of label bound to individual cells or solid supports are microscopically determined, and compared with the amount of label that is not bound to individual cells or solid supports. The degree of inhibition or binding is determined using this data. Confocal microscopy, and subsequent data analysis, allow the assay to be carried out without any separation step, and provide for high throughput screening of very small assay volume using very small amounts of test compound.

34 Claims, 22 Drawing Sheets

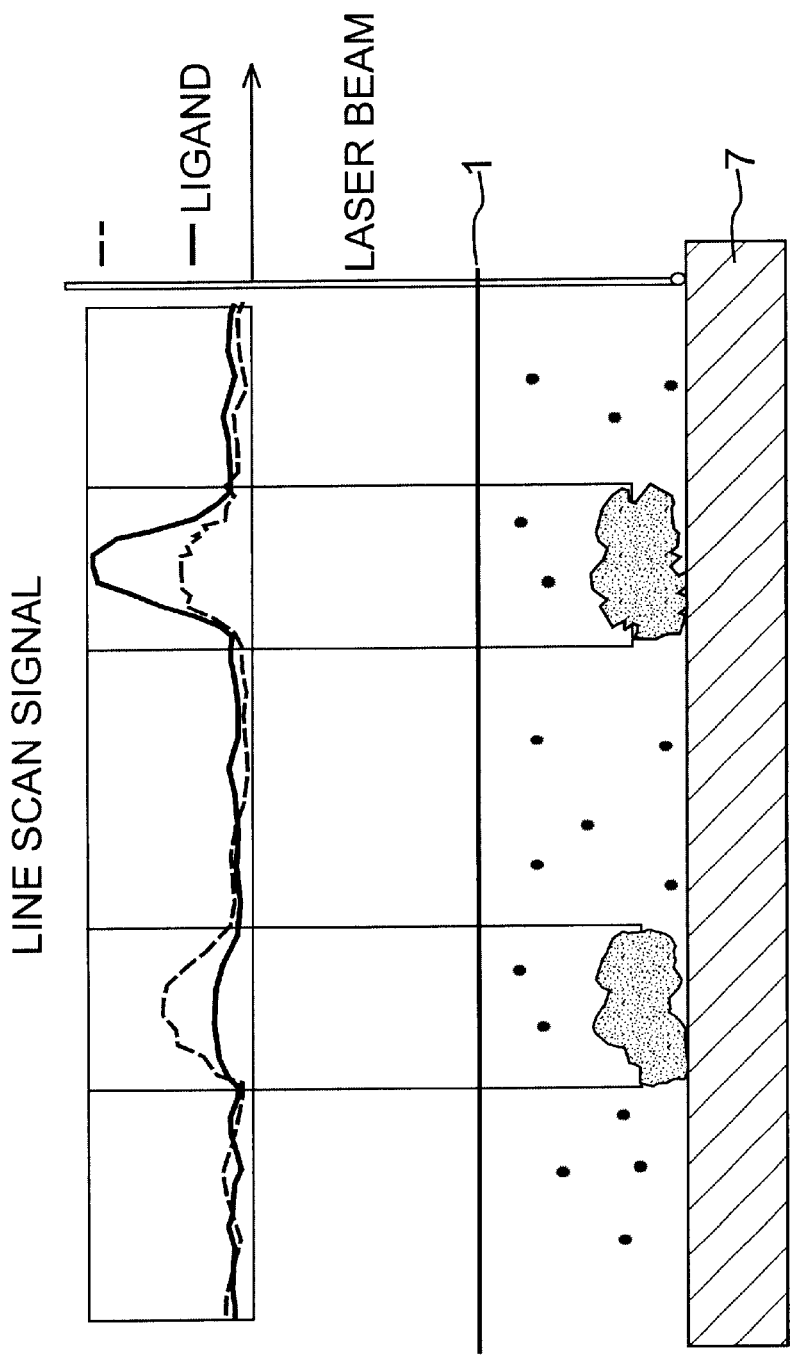

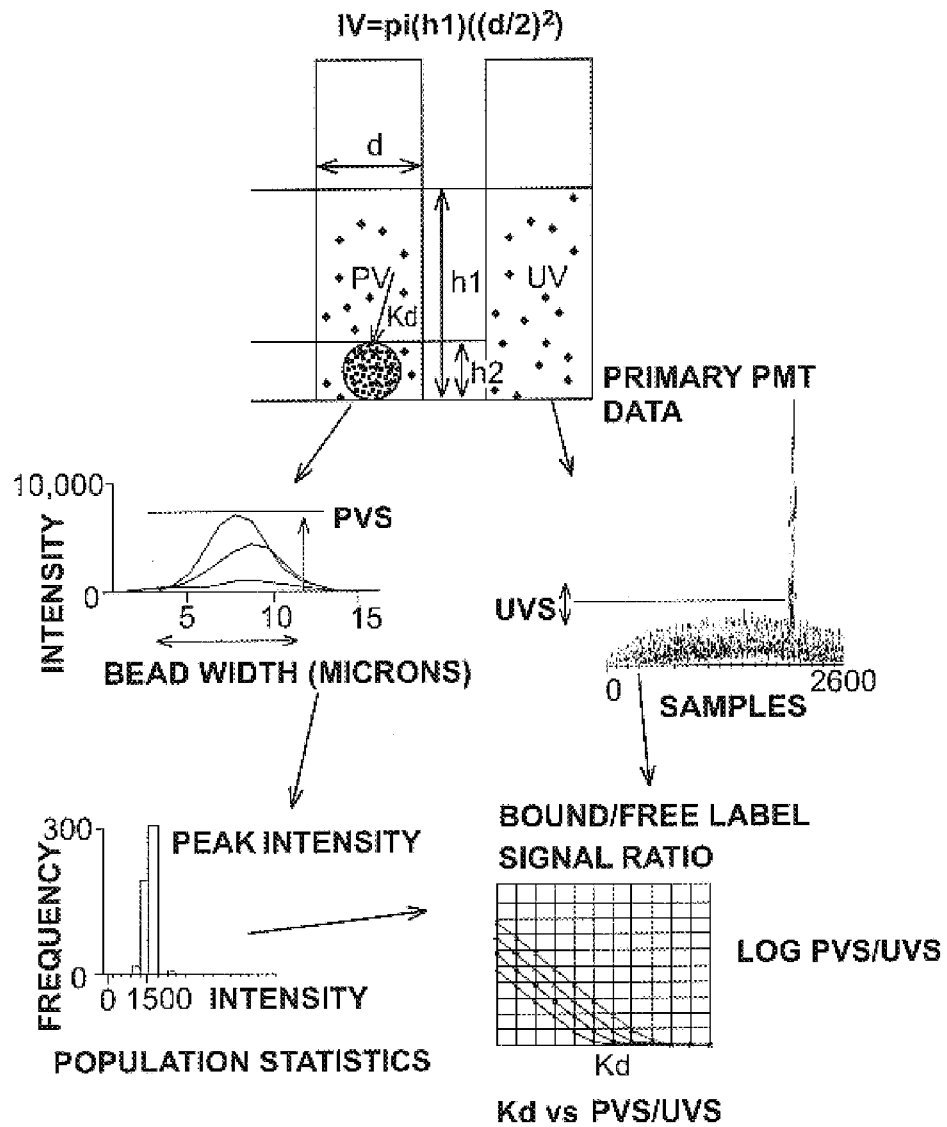

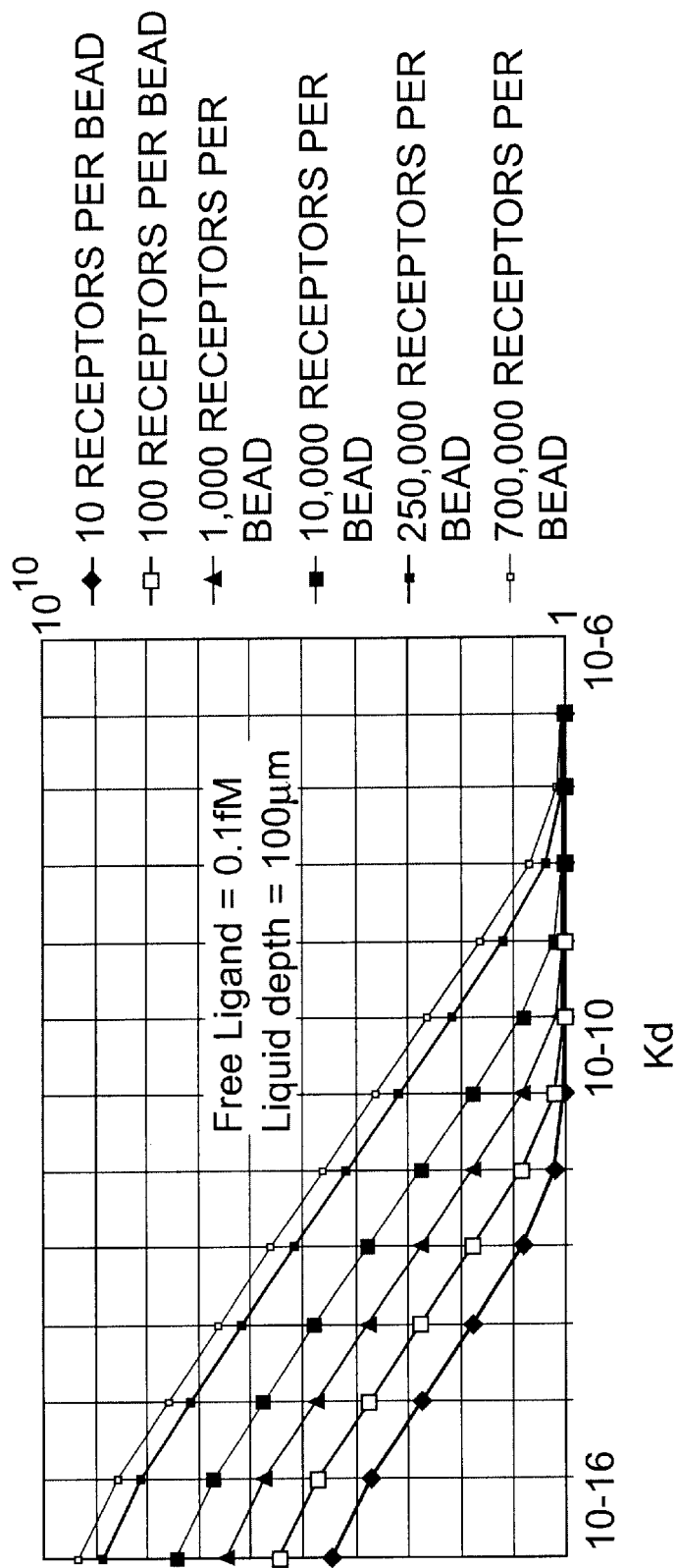
FIGURE 5: BOUND: FREE SIGNAL RATIOS FOR CONDITIONS WHERE THE RECEPTOR SITES ON A BEAD OR CELL ARE NOT SATURATED (LIGAND CONCENTRATION <<KD)

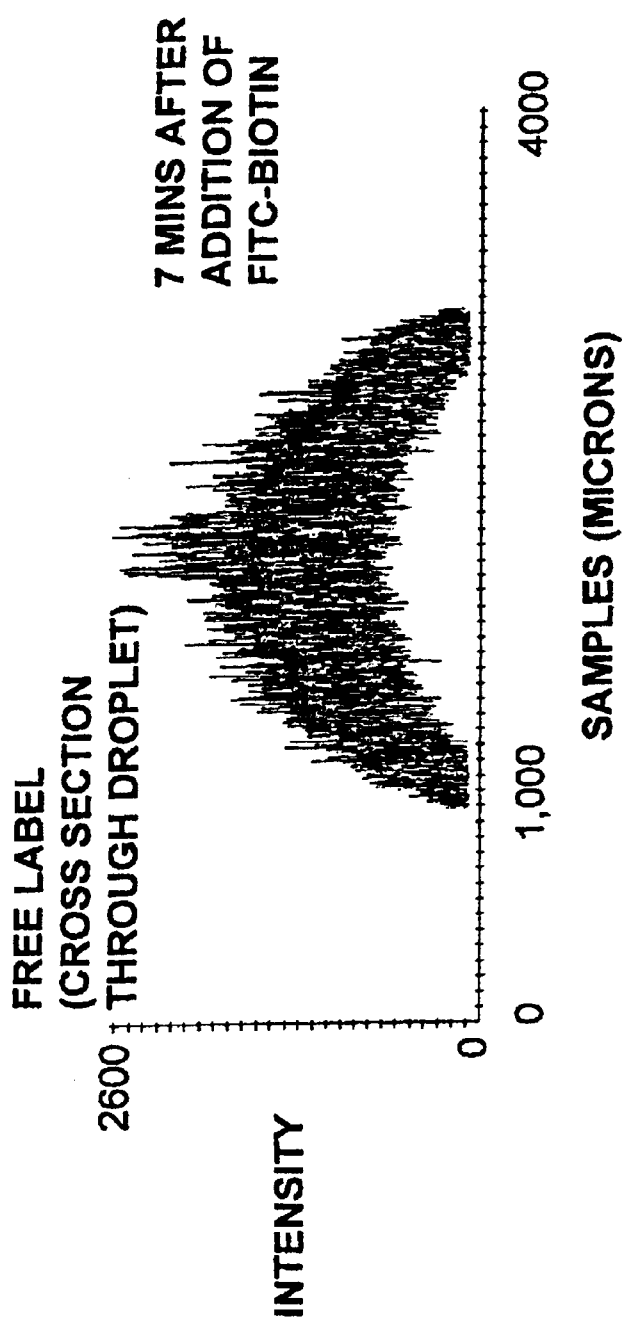

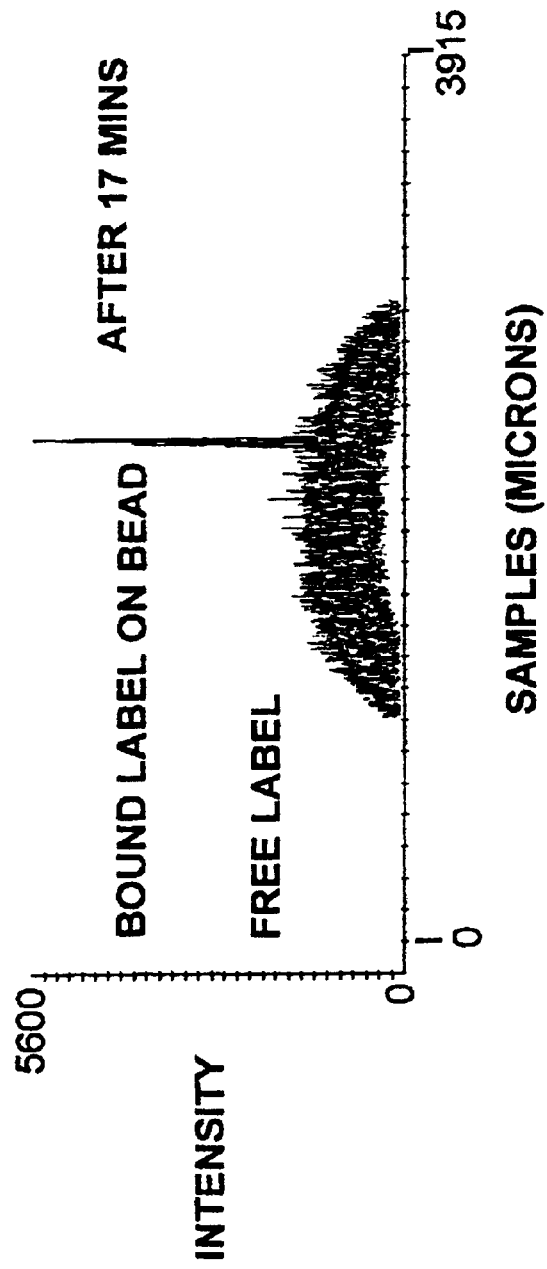
FIGURE 6B: TIME-COURSE SHOWING BIOTIN BINDING TO A SINGLE 2.8μm BEAD

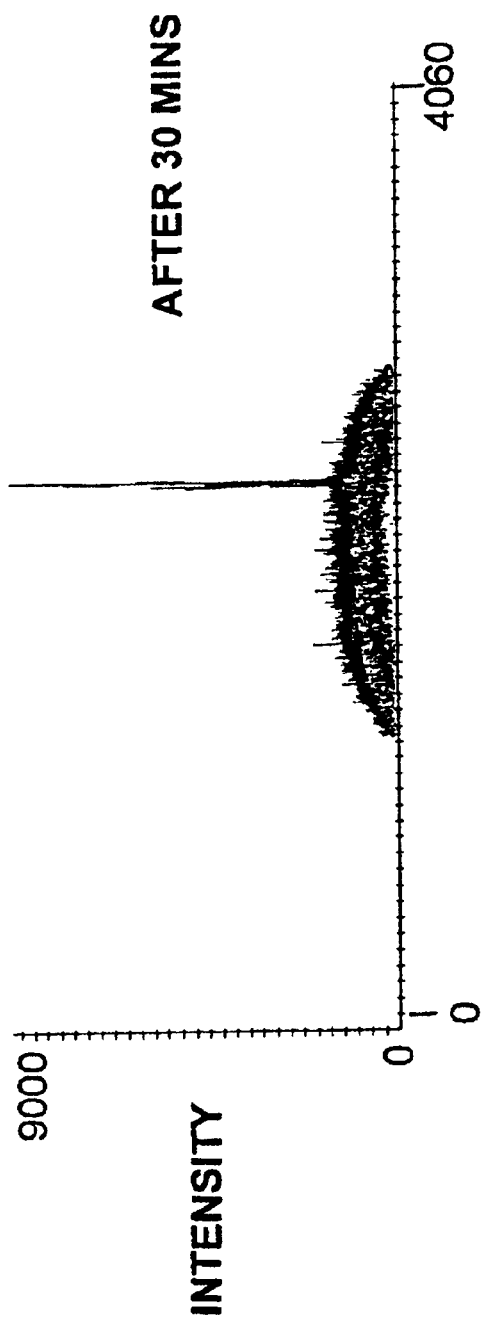
FIGURE 6C: TIME-COURSE SHOWING BIOTIN BINDING TO A SINGLE 2.8μm BEAD

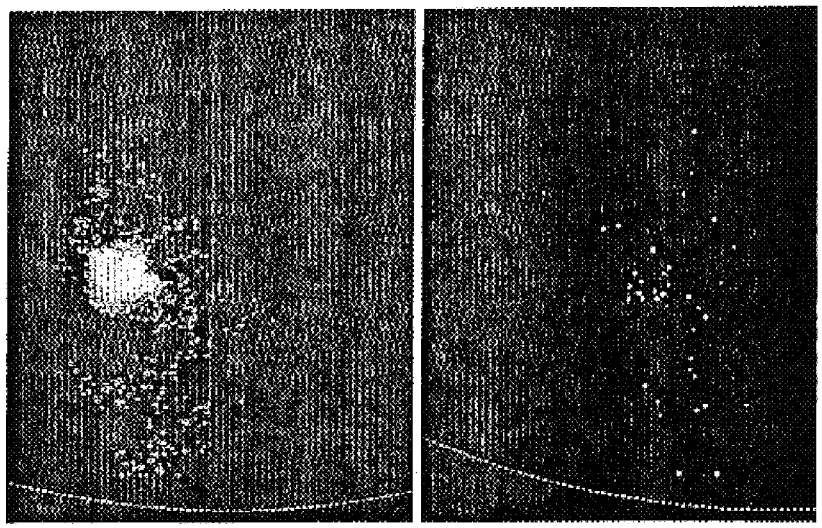
FIGURE 7: RAW DATA (LEFT) AND DISCRIMINATED DATA (RIGHT) FOR FITC-ANTI-TUMOUR NECROSIS FACTOR BINDING TO TUMOUR NECROSIS FACTOR ON THE BEADS
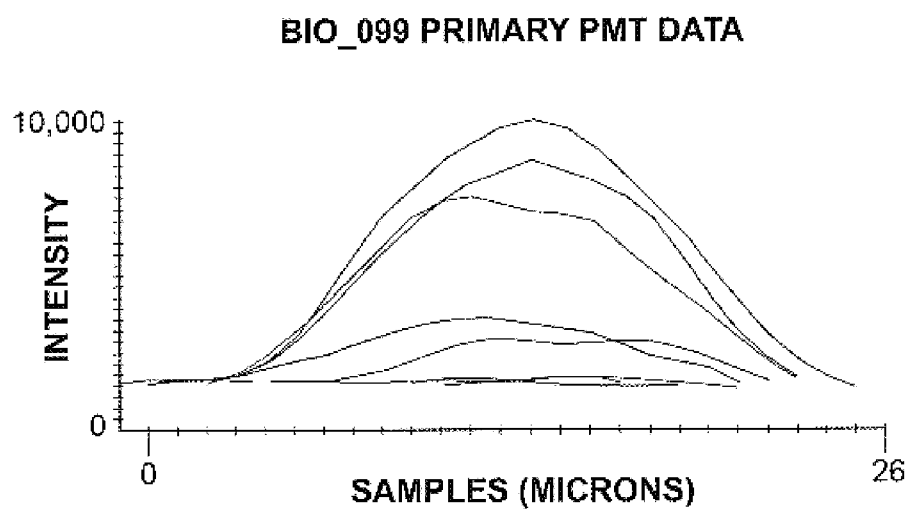
FIGURE 8: LINE AMPLITUDES FOR A SINGLE BEAD

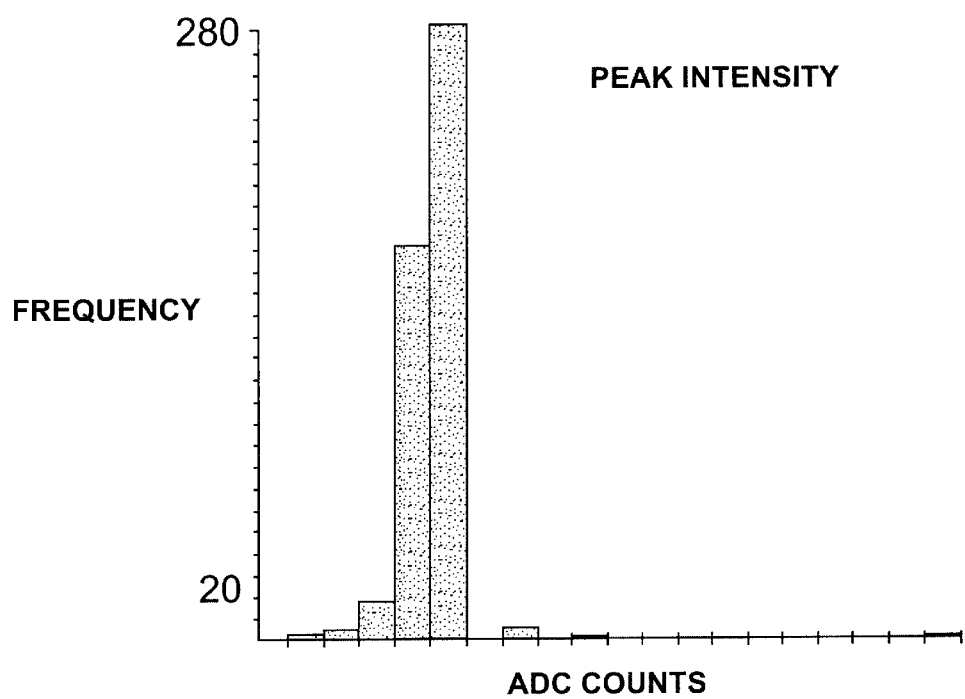
FIGURE 9: TYPICAL DISTRIBUTION OF PEAK INTENSITY VALUES FOR A POPULATION OF BEADS OR CELLS

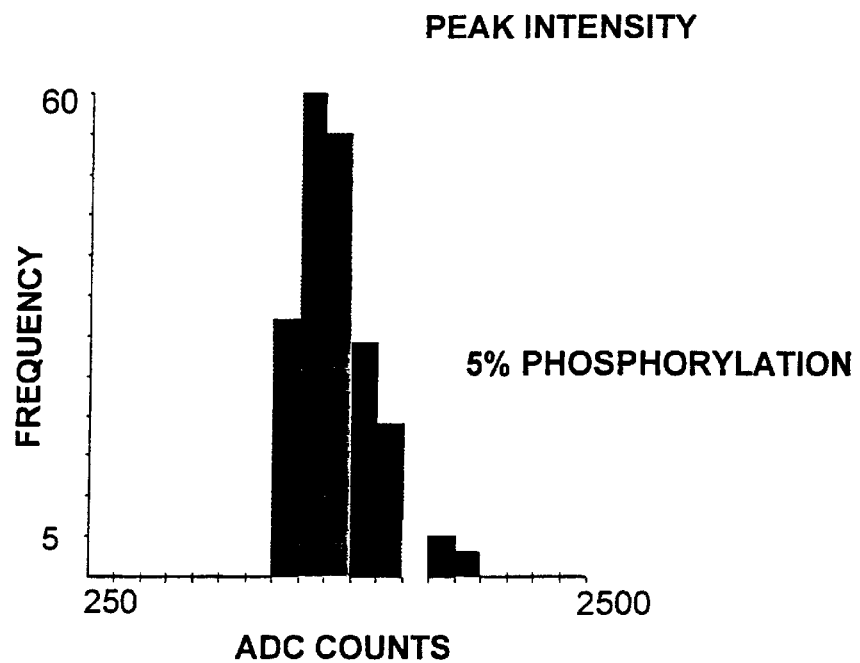
FIGURE 10: PEAK INTENSITIES FOR A POPULATION OF BEADS WITH SIGNAL JUST GREATER THAN BACKGROUND CONTAMINATION. (ON-BEAD TYROSINE KINASE ASSAY WITH BINDING OF FITC-ANTI-PHOSPHORYLATED TYROSINE ANTIBODY, BACKGROUND CUTOFF = 875 ADC COUNTS).

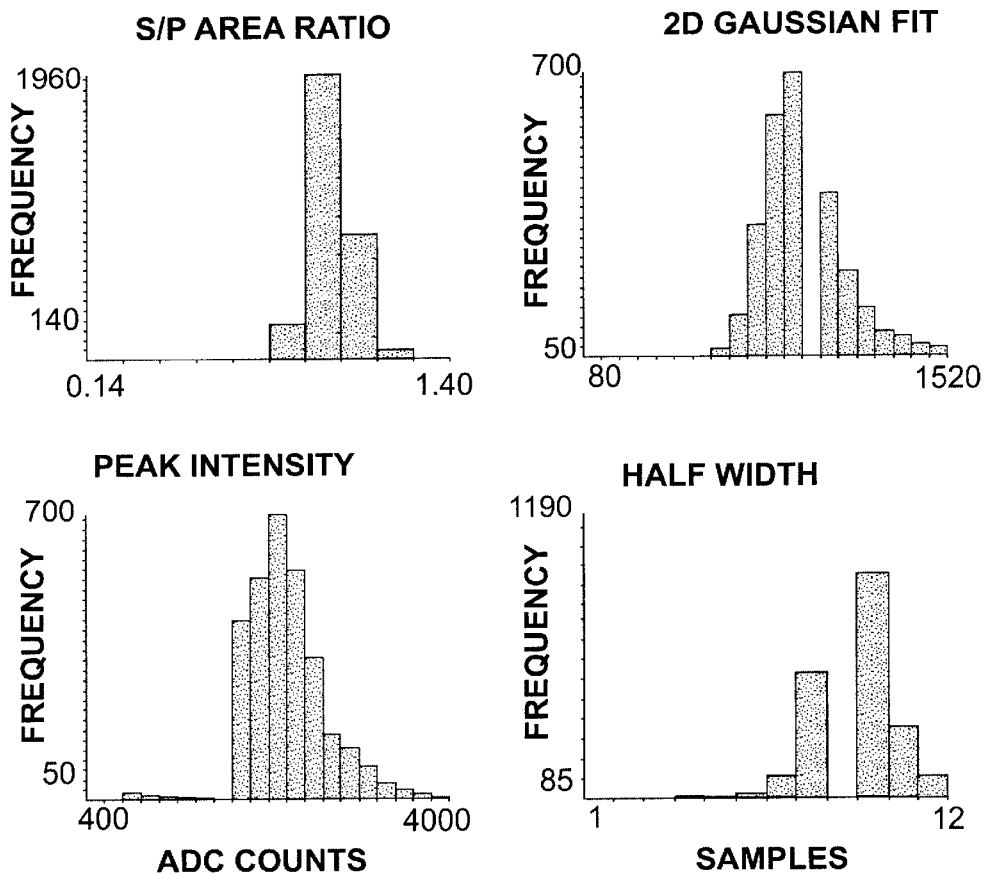
FIGURE 11: HISTOGRAMS FOR SECONDARY/PRIMARY RATIO, 2D GAUSSAIN FIT, PEAK INTENSITY AND HALF-WIDTH FOR A POPULATION OF BEADS IN A TYPICAL ASSAY.

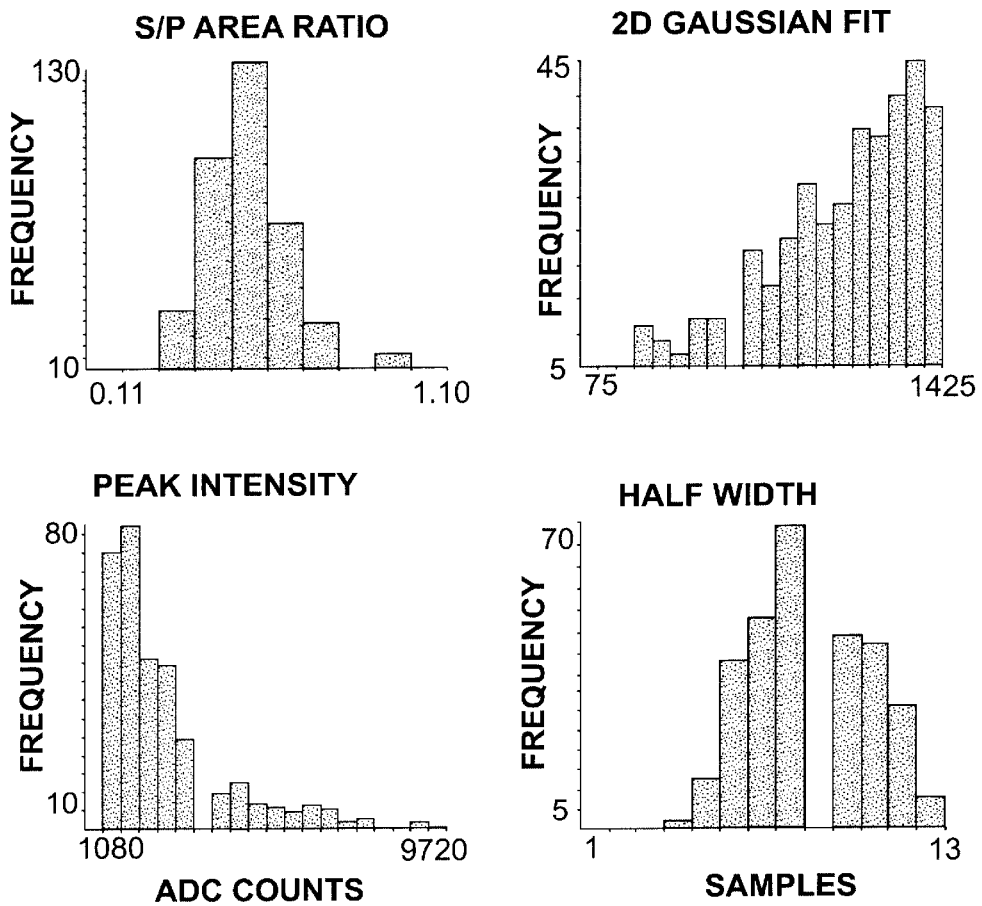
FIGURE 12: HISTOGRAMS FOR SECONDARY/PRIMARY RATIO, 2D GAUSSAIN FIT, PEAK INTENSITY AND HALF-WIDTH FOR CONTAMINATION IN A TYPICAL ASSAY. NOTE THE NON-GAUSSIAN DISTRIBUTIONS FOR PEAK INTENSITY AND 2D-GAUSSIAN FIT, AND THE BROAD DISTRIBUTION OF HALF-WIDTHS.

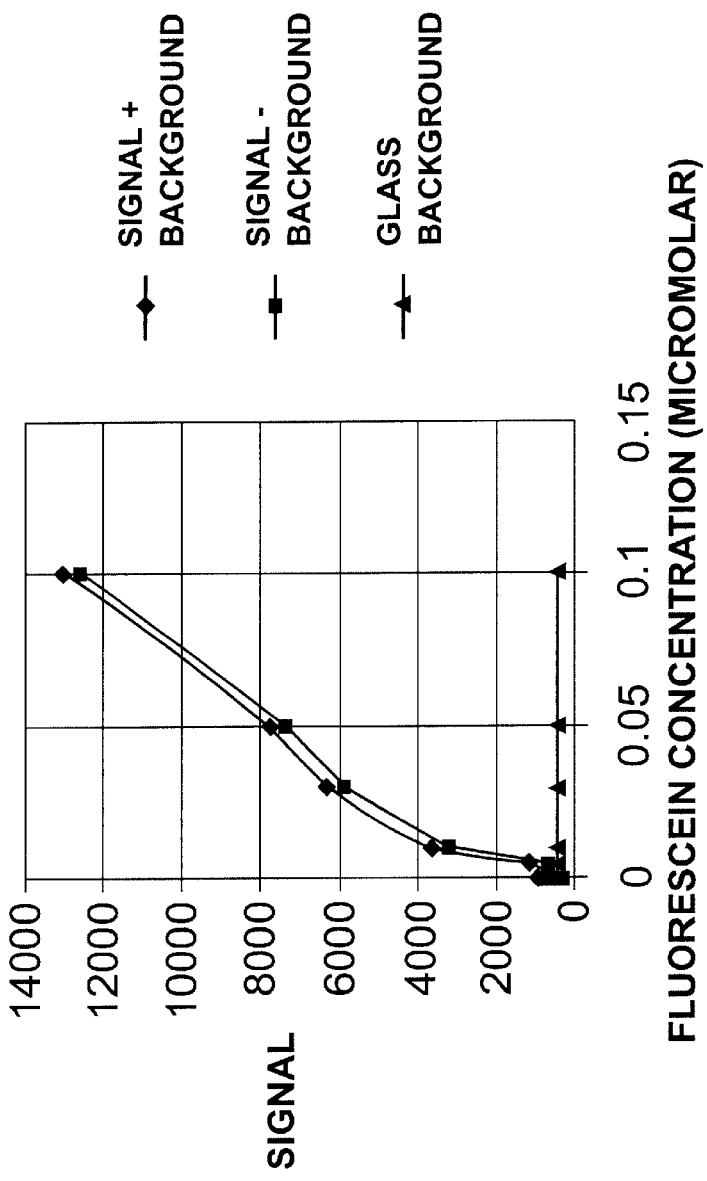
FIGURE 13: DETECTOR CALIBRATION. IN THIS EXAMPLE THE DETECTOR ELECTRONICS EMPLOYS A NON-LINEAR RESPONSE AT HIGHEST SENSITIVITY FOR A WIDE DYNAMIC RANGE.

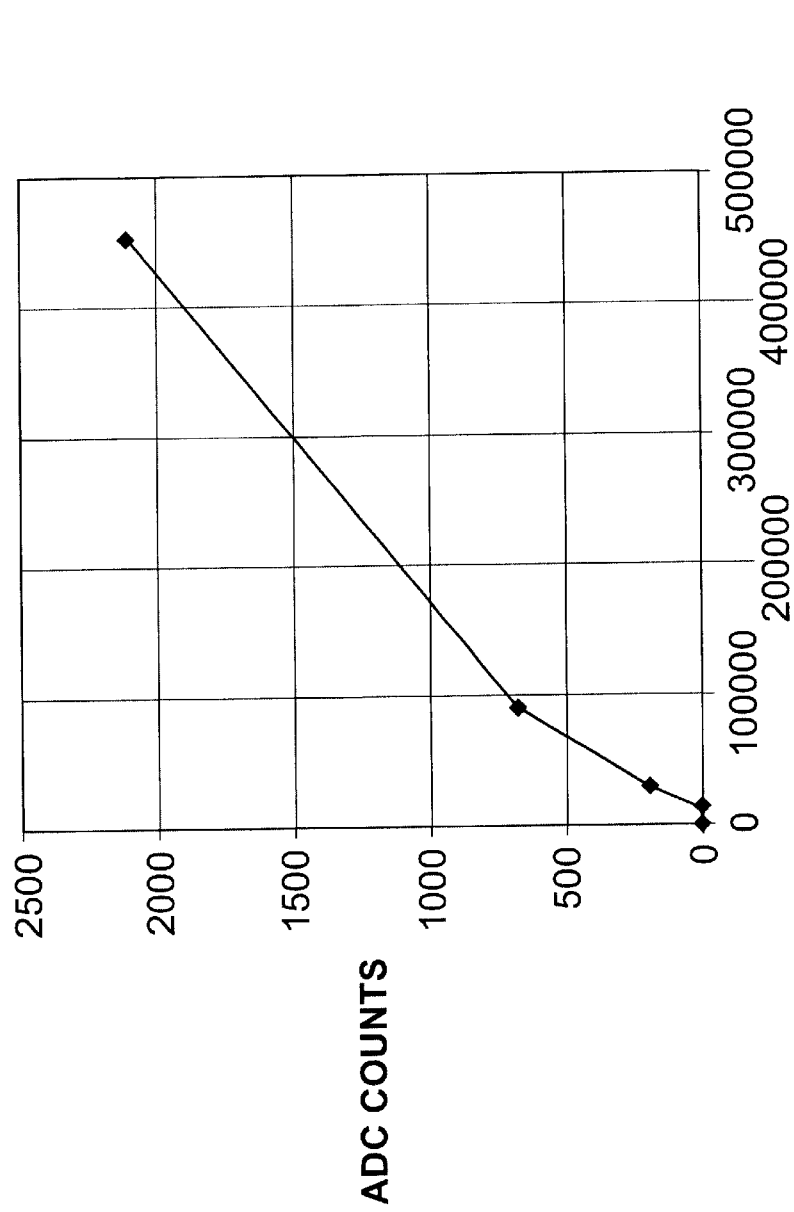
FIGURE 14: CALIBRATION OF DETECTOR WITH BEADS OF KNOWN SIZE AND FLUORESCEIN CONTENT.

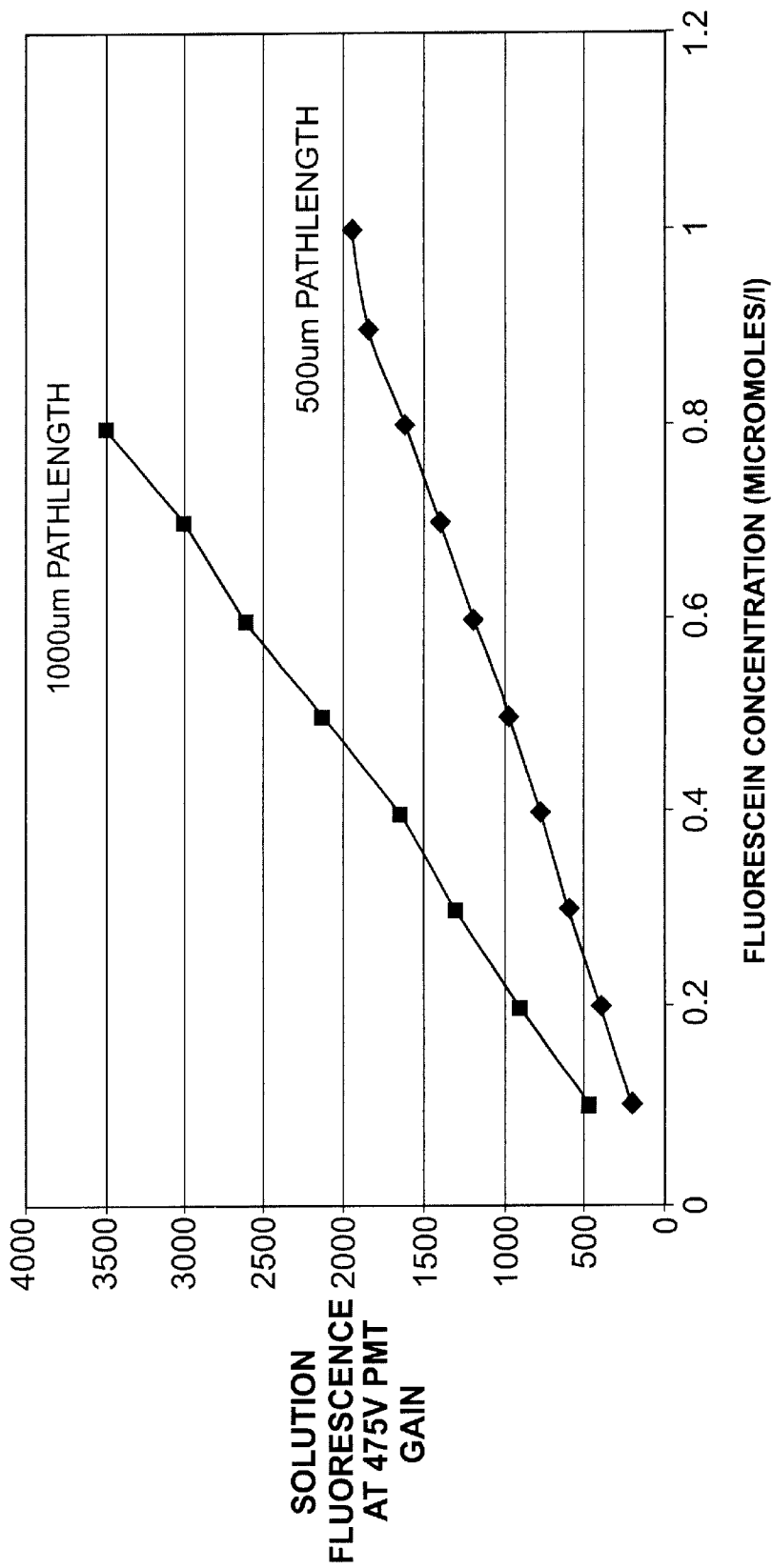

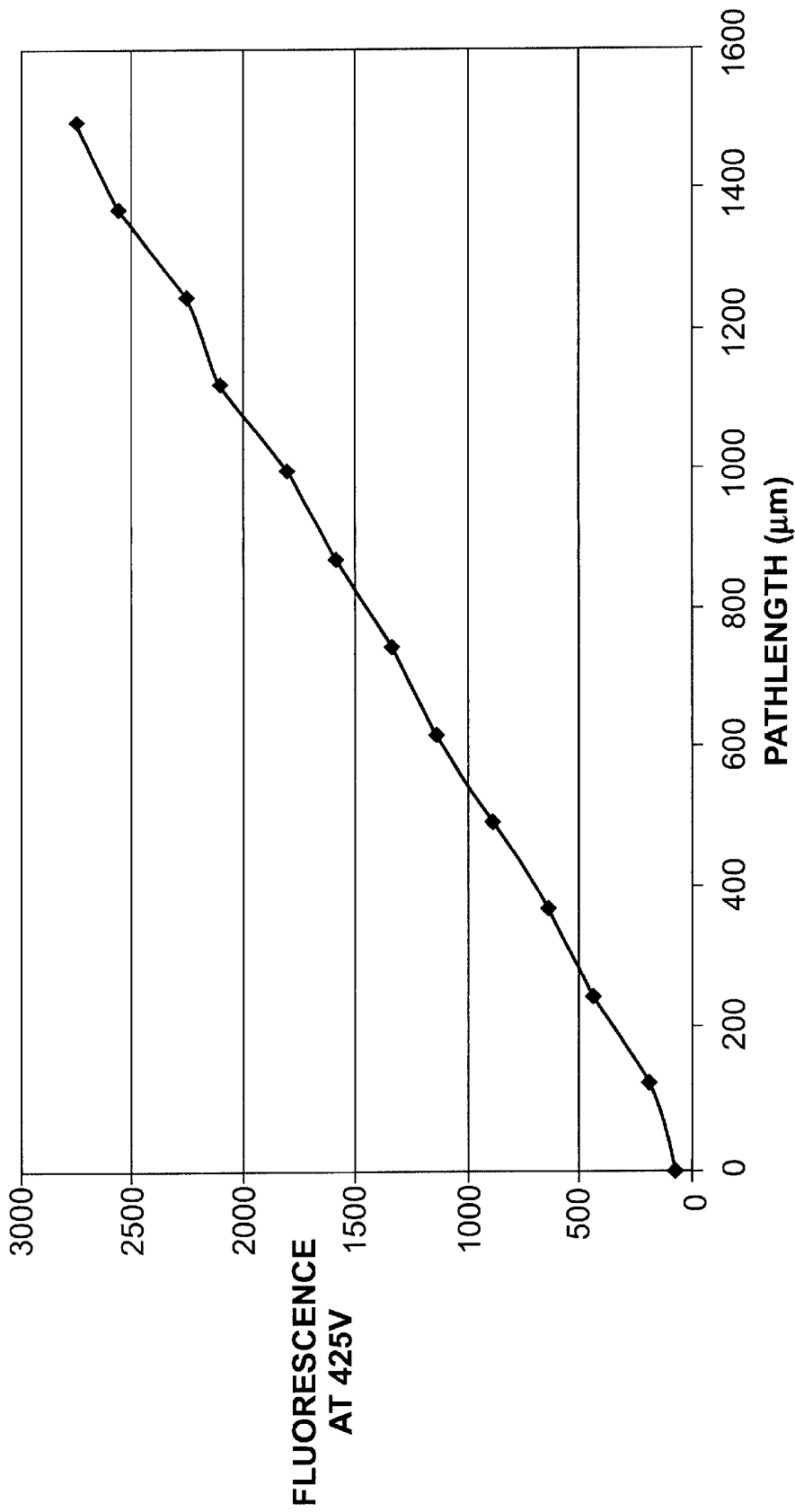
FIGURE 16. FLUORESCENCE VS PATHLENGTH FOR A MICROMOLAR FLUORESCEIN SOLUTION AT 425V PMT GAIN

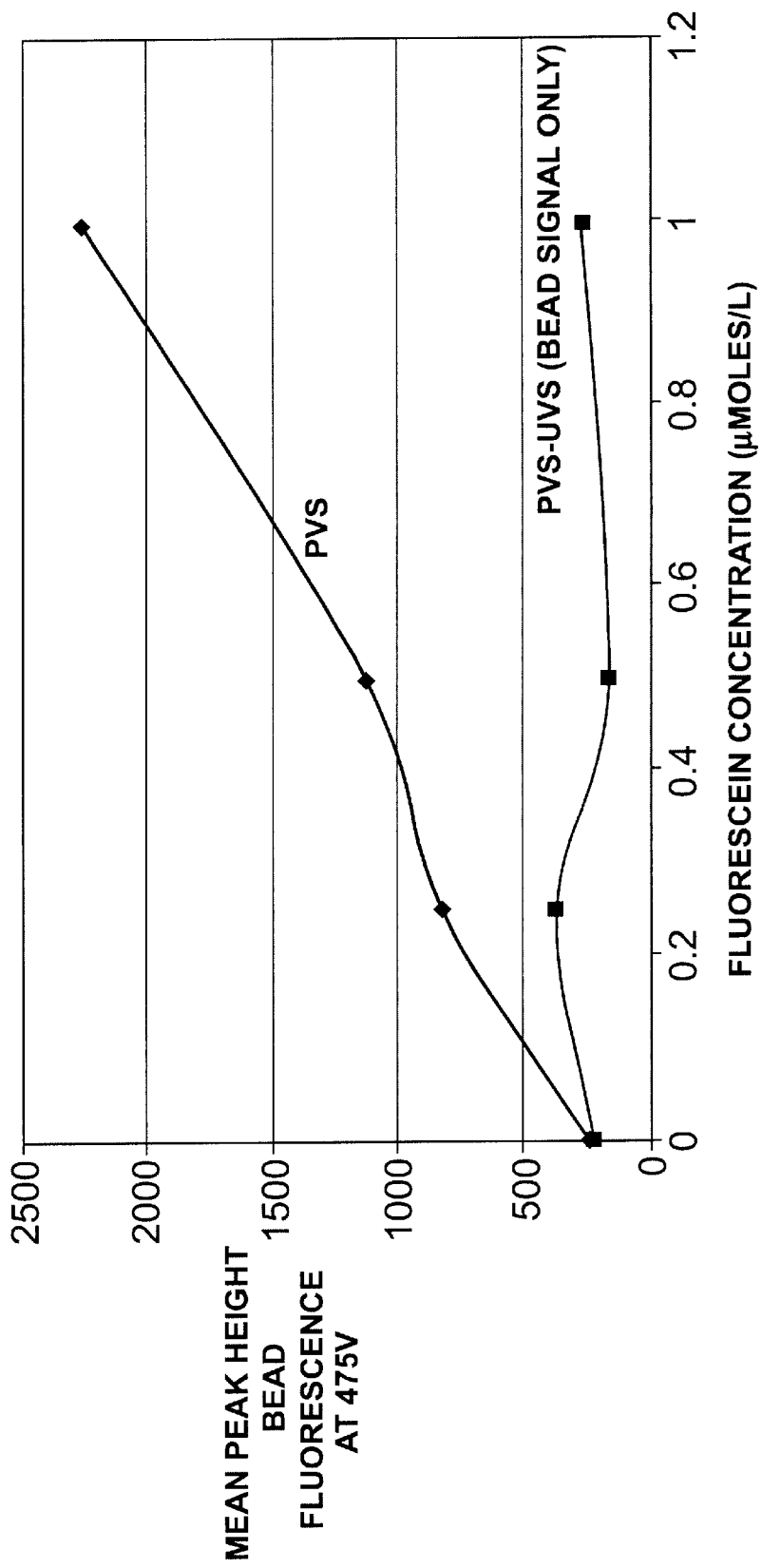
FIGURE 17. MEAN PEAK HEIGHT BEAD INTENSITY VS FLUORESCEIN SOLUTION CONCENTRATION FOR 450,000 MESF BEADS IN FLUORESCEIN SOLUTIONS AT A DEPTH OF 20μm, UNCORRECTED AND SOLUTION INTENSITY CORRECTED.

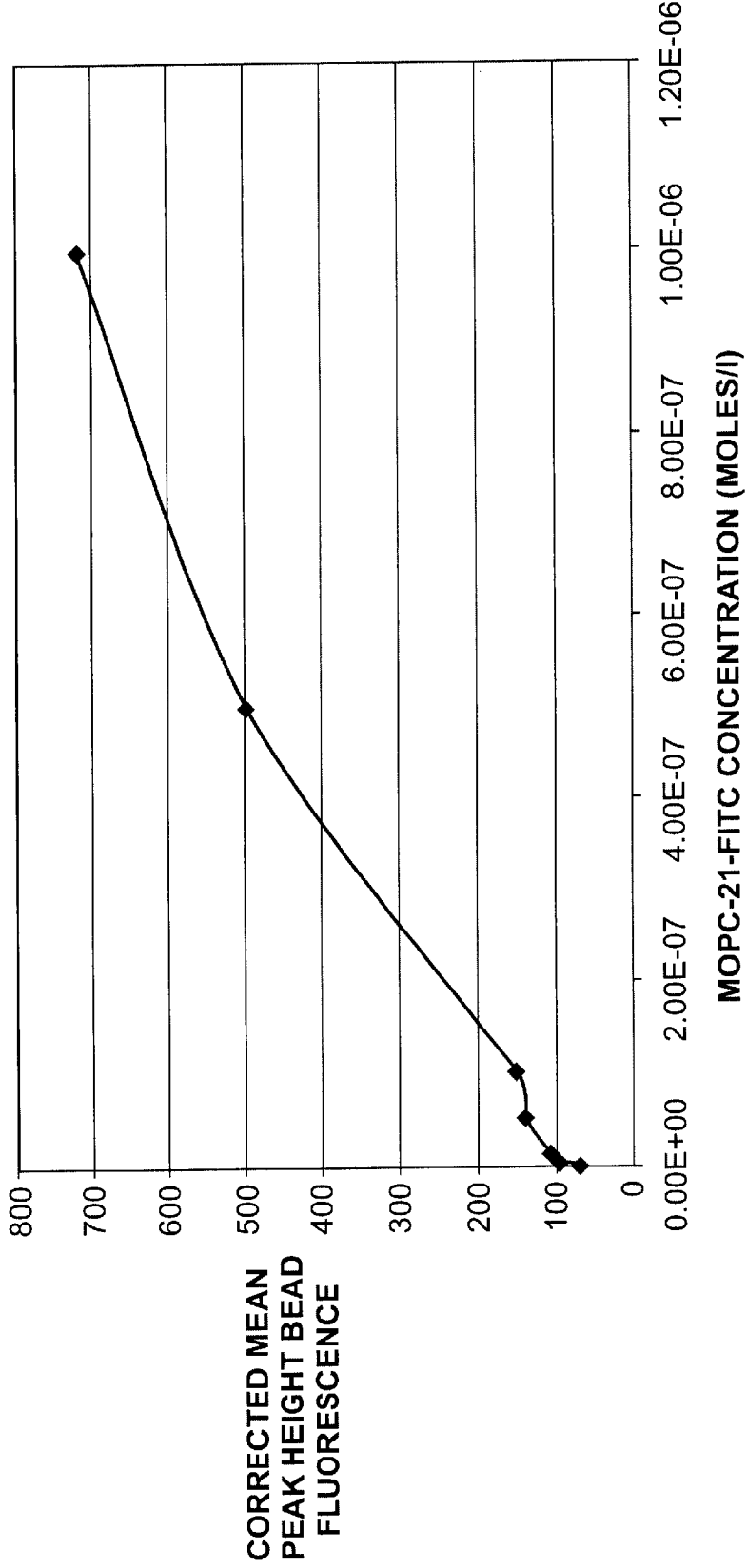
FIGURE 18. CORRECTED BEAD INTENSITY VS MOPC-21-FIT CONCENTRATION FOR GOAT ANTI-MOUSE BEADS AT 507V PMT GAIN. ALL DATA POINTS SHOWN

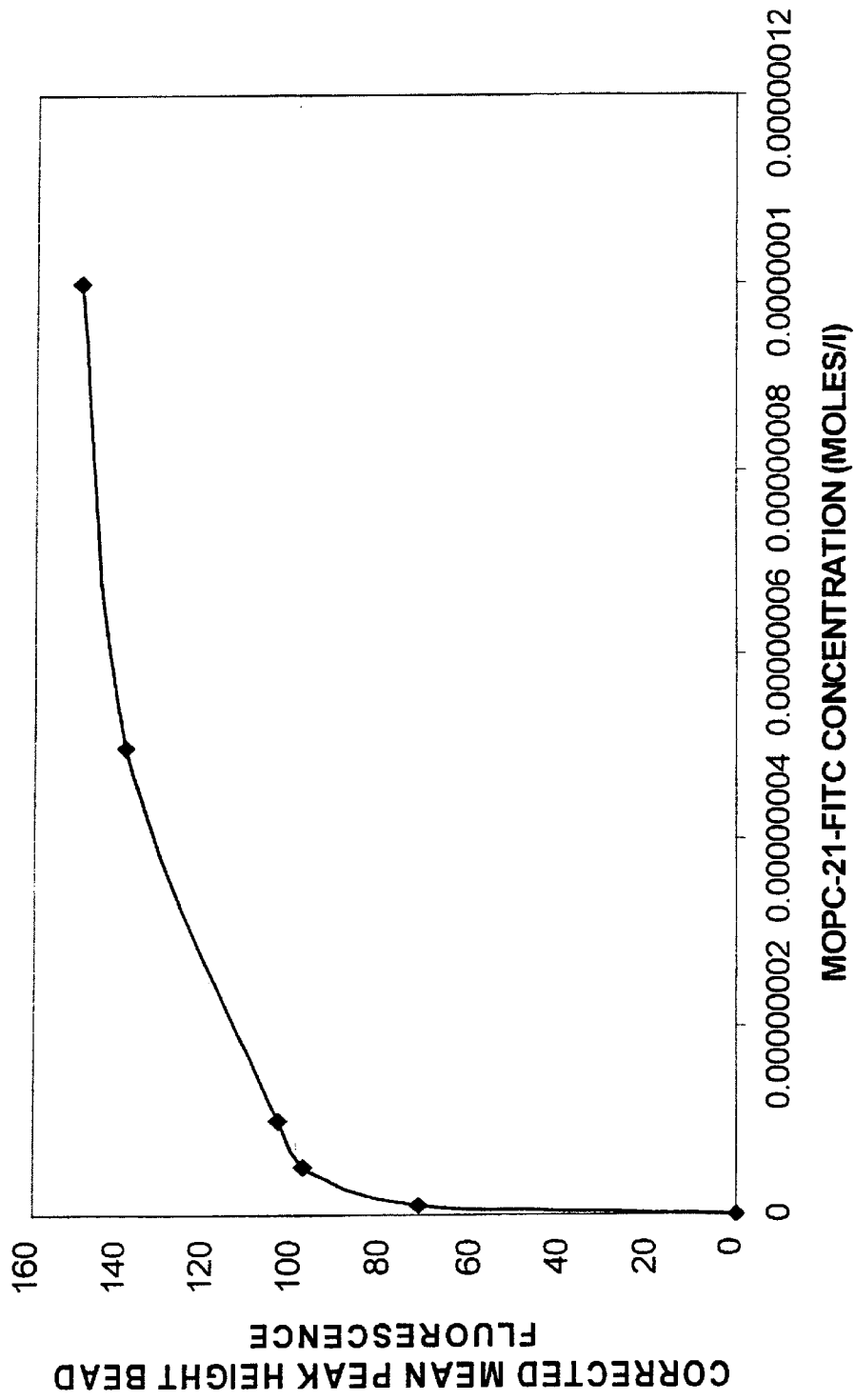

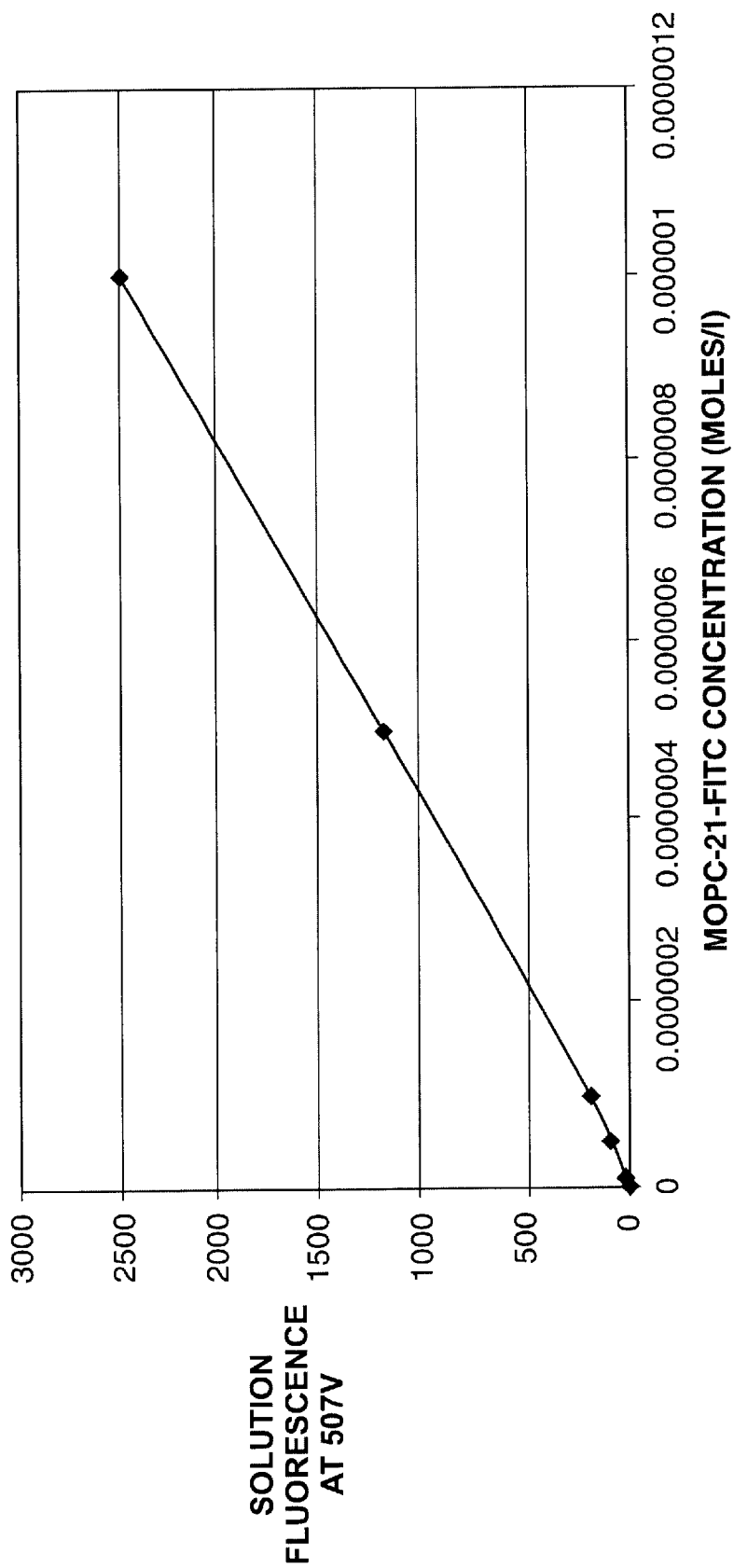

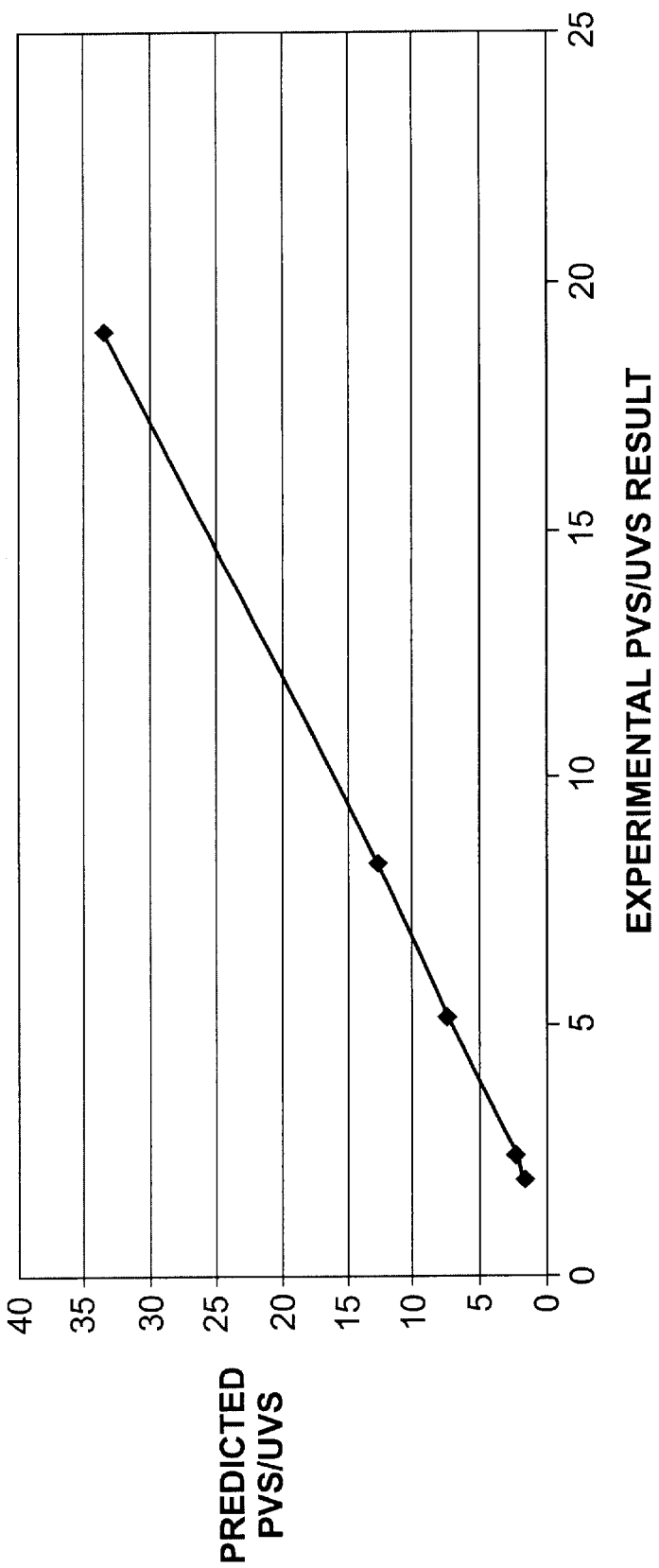

CHEMICAL AND BIOCHEMICAL ASSAY METHOD AND APPARATUS

The present invention relates to a method and apparatus for performing chemical and biochemical assays.

DESCRIPTION OF RELATED ART

The ability to characterize processes at a cellular or sub-cellular level is important in both drug discovery and clinical diagnostics. One class of interactions frequently studied is the binding of one biological molecule to another molecule, cell or part of a cell. This may be for example the binding of antibodies to antigens, hormones to receptors, ligands to cell surface receptors, enzymes to substrates, nucleic acids to other nucleic acids, nucleic acids to proteins, and viruses to cell surfaces.

Another class of interactions important in the biology of the cell are diffusion or transport of molecules or cells across membranes. This may for example occur by osmosis; via special transport proteins or through phagocytosis.

Many diseases are characterised by binding or transport processes. In drug discovery the aim is to identify a means of enhancing or blocking the process. In clinical diagnostics the aim is to detect abnormal function of these processes; the presence of abnormal nucleic acid material; or to identify foreign bodies (such as viruses or bacteria) to diagnose a disease so that appropriate treatment may be given.

The present invention seeks to provide a rapid and simple assay to detect and quantify binding and transport processes important in drug discovery and clinical diagnostics.

For the purpose of the following discussion "receptor" shall mean any biological molecule, cell or structure that binds another molecule, cell or structure. Similarly "ligand" shall mean any organic or inorganic molecule that binds to the "receptor". The discussion and examples will focus on the assay of a labelled ligand binding to a receptor. The prior art described and the invention can be extended to include the interaction of a non-labelled agonist or antagonist in a competition assay as commonly used in drug discovery.

The basic principle of a reversible binding reaction is described by the equation:

Dissociation Constant $(K_d) = [L] \times [R]/[L.R]$

Where [L]=concentration of unbound ligand at equilibrium, [R]=concentration of unbound receptor at equilibrium, and [L.R]=concentration of bound ligand/receptor complex at equilibrium The concentration is commonly measured in molar, and $K_d$ for ligand; protein interactions is typically in the range $10^{-4}$ to $10^{-15}$ $M^{-1}$.

The classical assay used in drug discovery and diagnostics is the separation assay. In this assay one component (for example the ligand) is dissolved or suspended in solution. The other component (for example the receptor) may be immobilised to a surface such as the walls of a well in a microtitre plate, or may be present on the surface of a cell. One or both components may have a label such as a fluorescent or radioactive marker attached to it to assist measurement with an instrument. The assay is performed by adding the soluble component to a well containing the immobilised component and allowing the binding of the components to come to equilibrium. It is not possible with conventional detectors such as colourimetric, fluorescent or radioactivity plate readers to directly determine the amount of bound labelled ligand in the presence of free labelled ligand. This problem is overcome by separating the free ligand from the bound ligand by decanting off the solution containing the free ligand. One or more washes with fresh solvent may be performed to remove any excess free ligand. A measurement of the remaining label is assumed to represent the concentration of bound complex in the original solution. This process may also be performed where the receptor is on a cell. If the cells are not attached to the well the washing process is performed in special filter plates that retain the cells, but allow the wash solvent to pass through.

This method works well where the rate of dissociation of the bound complex is slow, and indeed it is used with success in many assays. However, there are significant disadvantages to this assay method when applied more widely.

If the rate of dissociation is fast some of the bound label will be released back into the wash solution resulting in an error during reading. The efficiency of washing itself may vary from one sample to the next, reducing the repeatability of the assay. It is desirable to reduce or eliminate washing steps in automated systems to increase throughput, reduce complexity and eliminate the risk of cross-contamination between samples.

A number of non-separation assay techniques have been developed in recent years to overcome these problems including Scintillation Proximity Assay (SPA), Fluorescence Polarisation (FP), Fluorescence Correlation Spectroscopy (FCS), and Time Resolved Fluorescence (TRF). However, each of these techniques has disadvantages that limit their applicability.

SPA relies on the transfer of energy from a radiolabelled ligand to a scintillant bead onto which the receptor is attached. The assay has to be conducted at relatively high concentrations to produce enough signal. Legislation on the disposal of radioactive material and the risk of exposure to operators has led to companies seeking alternatives. SPA is not suited to some assays using whole cells and cannot be used to assay receptors or proteins inside cells. This means that functional receptor must be isolated from the cell to perform the assay, and this is costly, difficult and in some cases cannot be achieved.

FP is a technique for estimating the mass of a fluorescent object from its speed of rotation or translocation through diffusion. The sample is illuminated by a burst of polarised light and emitted fluorescence is measured in the same or other polarisation plane. If the label is bound to a large object, rotation or translocation will be slower and emission will be in the same polarisation plane as the excitation for some time after the illumination. If the free label is much smaller than the bound complex the molecule may more rapidly move out of the plane of the incident polarised light and emit in another plane. Provided that the fluorophore has a sufficiently long decay time, the light reaching the detector will take longer to decay after excitation if a substantial number of fluorophore-labelled ligands in the solution are bound to larger molecules.

The method is a correlation rather than a direct measurement of bound to free label. Some of the free label will emit in the same plane as the excitation. It also requires that the labelled ligand be very much smaller than the receptor and that decay time for the fluorophore be longer than the speed of rotation of target molecules. This technique has many drawbacks: it is difficult to differentiate non-specific binding and contaminating background fluorescence from specifically bound labelled ligand; it cannot be used to study intracellular interactions; the sensitivity of the method is reduced by relying on the decay of the signal rather than peak fluorescence and it is limited to the use of certain fluorophores.

FCS is similar to FP with the exception that FCS performs correlations on single molecules. The technique predicts the size of a fluorescent particle or molecule from its speed of translocation through a fixed laser beam by brownian motion. To perform the technique it is desirable that only a single molecule of fluorophore be present in the laser beam at one time. There is a practical limit to how narrow the laser beam can be (typically of the order of a few microns in diameter). It is also impractical to have extremely short path lengths through the fluid. For this reason FCS is usually performed with very low concentrations of label. This technique is highly susceptible to contaminating background fluorescence typical in practical assays. It is also comparatively slow, taking up to half an hour of continuous measurement to detect binding to larger molecules.

The technique of FCS has been known for more than twenty years. The difficulties of using it for practical assays has prevented its use until comparatively recently. Some of the drawbacks of the technique are: fixed beam FCS examines only one interaction at a time which may not be representative of the whole sample; it cannot differentiate directly between specific and non-specific binding; the technique requires running assays at very low concentration, which can bring additional problems such as loss of signal through non-specific binding of the label or receptor to the walls of the vessel and low signal to noise ratio as a result of low signal strength. The technique is also susceptible to thermally induced eddy currents. These severe limitations could be reduced by employing an established technique used in the study of flow in liquids. By scanning the laser beam it would be possible to take a snapshot of the location of a number of fluorescent particles. Subsequent snapshots could determine the speed and direction of translocation of these particles and hence their mass. However, many of the fundamental limitations of the technique listed above would still apply.

TRF is similar to SPA in that it relies on the transfer of energy from one molecule to another in close proximity. In this case energy from one fluorophore is transferred to another fluorophore in close proximity. The technique requires both the receptor and the ligand to be soluble and that a fluorophore be present on both the ligand and the receptor. This is not suitable for assays where a soluble receptor cannot be obtained, and in addition chemically modifying the receptor by the addition of a label can be difficult and lead to a reduction or elimination of activity.

Over the past several years a number of instruments and techniques have been introduced for low throughput screening of cells based on imaging techniques using microscope objectives and/or CCD cameras. Typical of these are flourescent microscopes and scanning CCD systems. These systems employ a light source to alluminate a clear-bottomed plate from below. Cells are grown or deposited in the bottom of the wells and a fluorescent label or reagent is added to the solution above the cells. The detector is focussed only on the bottom of the well (in the cell sheet) to avoid obtaining signals from the bulk solution containing free label. The sample is imaged onto a CCD array and the resulting frame analysed for brightness by software. This approach can be used to image fluorescence within or binding to cells or beads, but there are several drawbacks, which limit its use for quantitative assays.

A CCD has finite resolution. The largest CCDs available today have around 1 million pixels, but cost-effective devices used in scientific devices have significantly fewer. There is therefore a compromise between field of view and resolution. This means that typically the field of view is only 1 mm$^2$ with resolution of 4 $\mu$m at best. This is only sufficient to obtain poorly resolved images of around 100 cells at once, which is insufficient for obtaining statistically significant results in some assay types. The resolution is insufficient to allow accurate measurement of the size and shape characteristics of cells or beads. The sensitivity of CCDs is substantially less than PMTs, making them insufficiently sensitive for making quantitative measurements at low light levels (for example labelled ligand bound to cell surface receptors on cells where expression is low, perhaps only 5,000 receptors per cell). It is necessary for quantitative competition assays to be able to measure bound fluorescence well below saturation, and CCD imaging systems lack this ability. Each pixel of the CCD array has a different sensitivity, so measurements across the scan are not consistent. Each pixel can only detect one colour at a time. Multi-colour images may be obtained by using a filter wheel in front of the CCD array, and taking multiple frames with different filters. This slows down the reading time, and if the sample moves during measurement (as free cells and beads are likely to do in liquid) the spectral information is lost. Multiple CCD arrays can be used to collect images in multiple colours, but it is not possible to achieve perfect pixel alignment between detectors or to have true simultaneous multi-wavelength detection. CCD arrays do not exhibit uniform sensitivity across the visible range. It is very important for background rejection at low signal levels that true simultaneous spectral measurements are made.

CCD arrays are not capable of repeatedly scanning an area at rates fast enough to perform measurements of rapid transients or time resolved fluorescence techniques (nanosecond to microsecond sampling rates).

Some systems, such as the "FLIPR" from Molecular Devices and FMAT from Perkin Elmer scan the sample with a laser. These systems employ confocal optics to deliberately limit the depth of the field of the detector, thus minimising the background signal from free label. This signal is not used to measure bound:free label concentrations. Additionally, resolution of these systems is too poor to allow accurate measurement of the shape or size of small beads or cells.

All the imaging systems do not attempt to measure the concentration of free label. For assays resulting in a dynamic equilibrium such as receptor/ligand binding assays it is necessary to have a measurement of both the free and the bound ligand to calculate the equilibrium constant or related measurements such as IC50. This is particularly important in practical assays where variability in the liquid handling devices and the effect of evaporation can mean that the concentration of ligand in the assay does not correspond with the desired concentration.

In addition to the limitations described for each technique there are general drawbacks with all these techniques for application across the widest range of assays. With the development of high throughput screening it is important that as many types of assay as possible be carried out in a single system. Each of the above techniques needs its own detector. This often leads to screening teams having to bolt different detectors into their robotic systems when changing from one assay type to another. This involves down time, and typically also involves re-programming of the robotics.

Fluorescence detection is becoming the method of choice for drug discovery because it offers sensitivities approaching that of radio label assays without the health risks and disposal problems. The present embodiment, offers a practical solution to the problems discussed above.

BRIEF SUMMARY OF THE INVENTION

According to the present invention there is provided a method of performing a non-separation assay for determining the level of binding of one component to another, the method comprising the steps of:

providing a first component in solution;

providing an array of sites onto or into which is placed a second concentrated component;

immersing the array of sites with the solution;

scanning the array of sites with an illuminating light beam such that the light passes through the solution whilst illuminating the sites;

determining the intensity of light received from each of the sites and solution at at least one wavelength during illumination; and using the received light intensity to determine a reference value representative of the solution alone and a value indicative of the amount of binding of the first component to the second component.

Applying mathematical computation to the signals received by the detector enables certain parameters to be determined.

The illuminating light may be generated by a laser beam. The received light may be light generated by fluorescence, and more than one wavelength of light may be received.

The received intensity may be employed to determine the size and/or volume of each site and the number of molecules bound to the site. The site may be formed by any surface or particle onto or into which a component may be concentrated, e.g. a cell, bead patterned surface or simply by a well.

The illuminating light may be arranged to illuminate from above or below the sample with the emitted light being detected from above or below the sample in any combination in such a way that the illuminating light illuminates both the site and a significant volume of the solution above or adjacent to the site.

The present invention also provides an apparatus for performing the above method.

An advantage of the present invention is that it can be employed to provide a reference value to the solution in which the sites sit so that the concentration of any fluorescent component in the solution may be measured (free component) and the number of molecules of any fluorescent component bound to the site (bound component) may be measured and compensation can be made for any signal from the free component that is coincident with the signal from the bound component so that an accurate value for the number of molecules bound to the site may be measured, and further, bound:free ratios may be estimated without need to separate the components. Furthermore, it is possible with the method and apparatus of the invention to determine not only the amount of binding but the area/volume of each site to ensure more accurate results.

The light source may scan the solution and sites in a linear fashion, with one scan overlapping the next, so that a continuous measurement of received light intensity can be provided. Data relating to the received light intensity may be filtered by employment of a fixed or variable threshold in order to reduce the amount of data required to be processed.

A further advantage of the present invention is that, by employing continuous scanning of the sites and solutions it is possible to determine accurately site locations and also to provide a reliable indication of spurious results caused by contamination and the like.

Yet another advantage of the present invention is that the meniscus of the sample may be determined simultaneously with the measurement of bound: free and compensated for in the mathematical analysis.

BRIEF DESCRIPTION OF THE DRAWINGS

One example of the present invention will now be described with reference to the accompanying drawings, in which:

FIG. 3 is a schematic side view of the method and apparatus of the invention being applied to two assay sites;

FIGS. 4 & 5 illustrates the basic theoretical elements of the invention;

FIGS. 6 to 14 are sets of graphs showing the outputs of an apparatus according to the invention at various stages during a process on which an assay is being performed; and FIGS. 15 to 21 are a set of graphs related to a third example assay providing assumptions in theory.

DETAILED DESCRIPTION OF THE INVENTION

Figure 1:
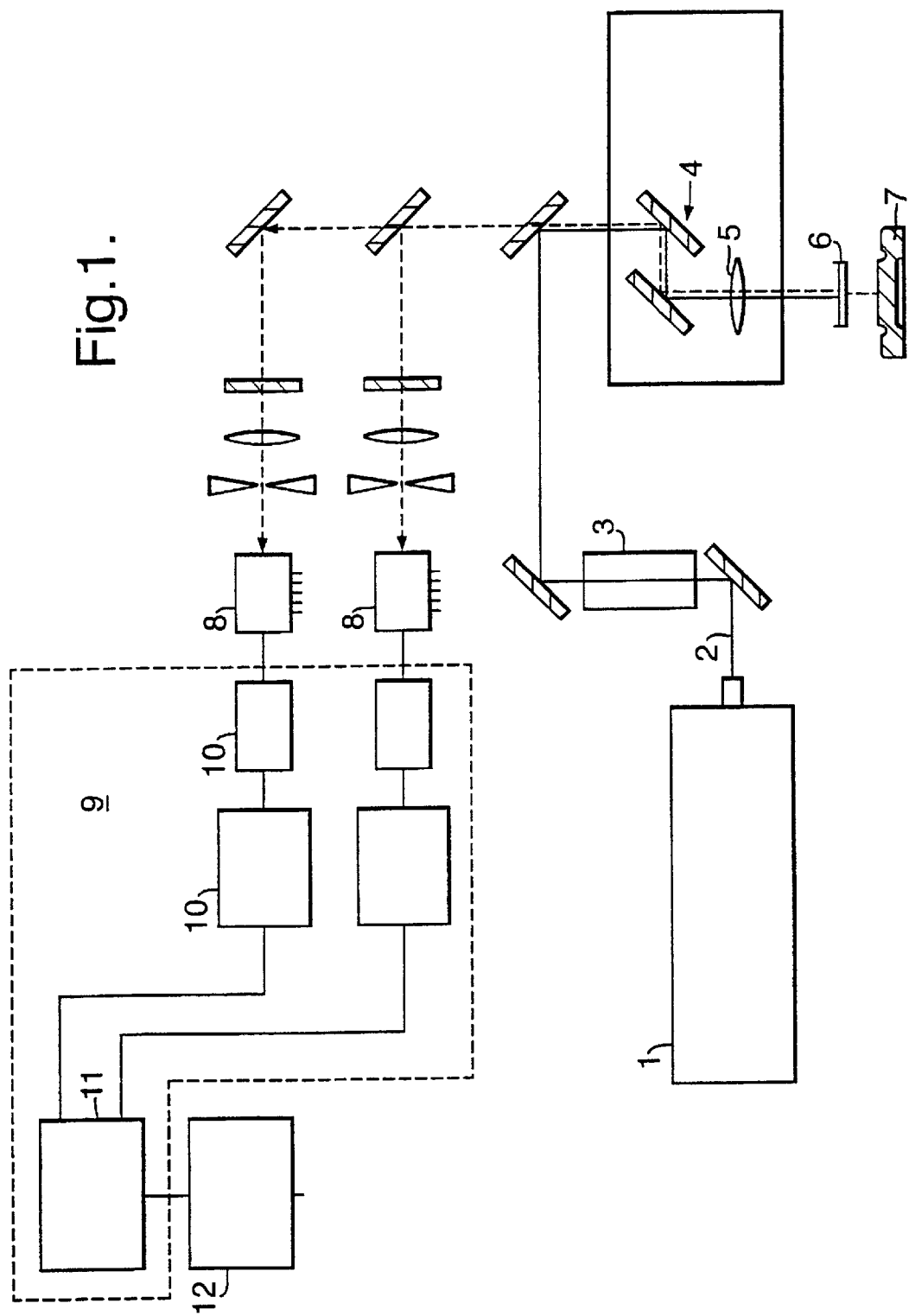
FIG. 1 is a schematic diagram of an apparatus that may be arranged to employ the present invention.

U.S. Pat. No. 5,66,3057 describes a method for rapidly detecting micro-organisms in water. The final process of this method involves scanning a laser across a membrane filter on which are retained fluorescently labelled bacteria. The system uses a combination of discriminants and threshold algorithms to pick out individual cells amongst the continuous background of free label and background fluorescence. The line amplitudes obtained for each cell is an accurate measurement of the fluorescence intensity of the cell and can be calibrated to give a measure of the amount of bound fluorophore. Some free label is always present from the labelling of the bacteria, however this is undesirable for bacterial detection and the method of U.S. Pat. No. 5,663,057 seeks to minimise this by arranging as far as possible to retain the label within the cells and additionally to minimise the liquid on the sample by the use of a porous membrane. For these reasons there is no defined and homogeneous layer of liquid present suitable for the measurement of a concentration of label in solution. The system measures the average background fluorescence. This data is collected for reference purposes and is not used in the detection of micro-organisms. FIG. 1 is a schematic diagram of a device employed in U.S. Pat. No. 5,663,057, but adapted to perform the method of the invention, this device will be described in more detail below.

Referring to FIG. 1, a laser 1 emits an illuminating light beam 2 which passes by a series of mirrors and a beam expander 3. The illuminating beam 2 is then directed via scanning mirrors 4 and a lens 5. The scanning mirrors 4 can be controlled to scan the beam 2 across the surface of a filter 6 and assay sample 7 in a manner that will be described below with reference to FIG. 2.

A telescope may be introduced at the beam expander position 3 to enable the spot to be focussed at different distances to the scan lens 5 or to control the size of the laser spot at the target.

Light from the assay sample 7 passes back through filter 6, lens 7 and mirrors 4 to one or more light receiving units 8, which in this example are photo multiplier tubes. Signals generated by the photo multiplier tube 8 are fed to an analysis 9, which include amplification and sampling electronics 10. The amplified and sampled signal is then forwarded to a data processing means 11, the operation of which will be described below. The output of the processing means 11 is fed to a display device 12, which may be a simple monitor or a personal computer.

Figure 2:
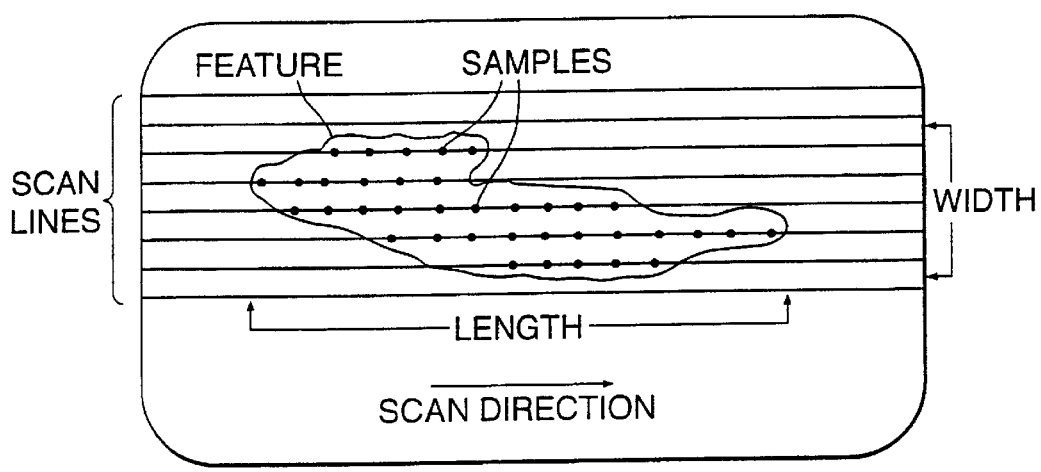
FIG. 2 is a diagram showing the scanning process of the apparatus of FIG. 1.

Referring to FIG. 2, it can be seen how the light beam 2 is scanned sequentially over the assay sample 7 so that the total sample surface area is covered. It is preferable for the scanning to be such that each adjacent scan overlaps the previous scan, ensuring that no features are missed. The processing means 11 can be configured to compensate for the overlap.

The operating principles of the system of the invention will now be described with reference to FIGS. 3 and 4. FIG. 3 illustrates how line amplitudes are obtained when a sample is scanned. FIG. 4 illustrates the principles of the assay.

EXAMPLE 1

For ease of illustration of a simple example of the invention we make a number of assumptions:
1. That the laser beam can be considered to illuminate a volume of: $\pi r^2 h$, where r=the radius of the beam (in our example 3 $\mu$m), and h=the depth of the liquid. We shall call this laser illumination volume (IV).
2. That the fluorophore solution is dilute, there is minimal quenching and that each molecule of fluorophore in the volume element emits with the same intensity.
3. That a cell or bead has a spherical volume and that all fluorophore molecules bound to that cell or volume exhibit equivalent fluorescence as they would in solution. We shall call this bead volume (BV).
4. That each bead or cell may be considered to represent a local concentration of receptor, being the receptor number divided by the bead volume.
5. We can see that where there is no bead or cell in the volume element ("unpopulated volume element") the detector reads the fluorescence intensity due to free label only. We call this intensity value "Unpopulated Volume element Signal" or UVS. Where a cell or bead is present in the laser volume element (a "populated volume element") the intensity signal will be made up of the additive intensities of the label concentrated on the cell or bead and the signal from the free label in the remainder of the volume element above the bead or cell. We shall call this signal the "Populated Volume element Signal" or PVS.

Whilst a person skilled in the art may consider these assumptions to be inaccurate, we have shown in example 3 and in FIGS. 15 to 21 that these assumptions are sufficient to allow the method to be reduced to practice with high correlation between observed and expected values.

It will be appreciated that the concentration of fluorescent molecules in the cell volume needs to be significantly higher or lower than the equivalent volume of solution in order for the system to detect a difference:

Signal Ratio $PVS/UVS = <1>$

In most cases we are aiming for PVS/UVS >1 to demonstrate binding of a fluorophore to a cell or bead. The brightness of the cell volume relies primarily on three factors: the number of binding sites (or receptors) on the cell or bead; the $K_d$ of the association, and the concentration of the labelled ligand in solution at equilibrium.

It can also be appreciated that the present invention can be used to measure the extent of binding or proximity of a fluorophore to a surface where that surface may modify the fluorophore or mask or quench the emission such that light output from the fluorophore is reduced or eliminated locally. Examples include, but are not limited to, the conversion of a fluorescent compound to a non-fluorescent compound by an enzyme; a reduction of fluorescence due to the presence of a quenching agent on a surface, bead or cell; translocation of a label into a cell and change in the spectral characteristics of a fluorophore.

If the concentration of free fluorophore is too great and/or the liquid is too deep it will not be possible to detect the labelled cell. Therefore, for practical assays these parameters must be kept within sensible limits. FIG. 5 gives predicted values for PVS/UVS signal ratios plotted against $K_d$ for the following conditions: 6 $\mu$m diameter bead varying indicated numbers of binding sites; 6 $\mu$m diameter laser beam; depth of liquid of 100 $\mu$m; and labelled ligand concentration at equilibrium of 1 nM.

With the assumptions made above it is possible to provide an estimate for the number of molecules or surface concentration of ligand bound to each bead or cell and the concentration of the free ligand. In this case:

[Free]$\propto UVS$

[Bound]$\propto PVS-(UVS.(IV-BV)/IV)$ where
Conc. of free label=[Free]
Conc. of bound label=[Bound]

This is a much-simplified case for illustrative purposes. In practice, it is necessary to correct for a number of factors such as depth of field, liquid depth, liquid meniscus, laser attenuation, quenching etc. Methods of correcting this model to improve the accuracy of measurement are given in later examples.

A practical example of the invention is now described.

EXAMPLE 2

A simple example of one embodiment of invention is shown in FIG. 6. A 5 $\mu$l sample of a solution of 48 nM fluorescein isothiocyanate-labelled biotin (FITC-biotin) is added to 5 $\mu$l of a solution of buffer containing a single 2.8 $\mu$m diameter bead coated with streptavidin (obtained from Dynal). The sample was presented to the instrument for scanning as a 10 $\mu$l droplet on the surface of a glass microscope slide. Illumination and light collection was arranged from above the sample. The instrument was set to take fluorescent intensity measurements at 1 $\mu$m intervals across the sample in the x-direction with a line-to-line step of 2.2 $\mu$m in the y-direction. As the laser spot size was 6 $\mu$mm, this allowed for overlap between each scan line. The graphs plot the relative intensity (analogue-to-digital converter or ADC counts) against position (sample number) for several adjacent scan lines. Initially, the FITC-biotin has had insufficient time to diffuse to the streptavidin sites concentrated on the bead. The sample was scanned at intervals over the period of the experiment. It can be readily appreciated that the signal obtained from the illumination will be proportional to the number of molecules of label (FITC-biotin) in the path of the laser at each point. If, as in this case, the label is homogenous throughout the droplet then the signal at each point is proportional to the path length of the laser through the sample. The top diagram clearly shows that each scan line represents a cross-section through the droplet, and that the droplet meniscus in this case is hemispherical as expected.

If the concentration of the label is known it is apparent that the volume and shape of a sample (in this case a droplet) may be estimated by calculation. It also follows that if the volume or height of a solution is known then, after calibration of the apparatus with known solutions, it is possible to calculate the concentration of free label from the intensity signals obtained.

With time, the FITC-biotin diffuses to the bead and is gradually concentrated on the surface of the bead (lower plots). In this experiment, equilibrium was achieved after 30 minutes. It can be seen that the signal on the bead is significantly higher than that of an equivalent volume of solution, and that the signal from this bead is added to the signal from the solution (PVS/UVS=approx. 6.1 at equilibrium).

Thresholding and Data Reduction

In Example 2 a measurement was made and data saved for every point in the sample. The Chemscan RDI modified for this application has three detector channels and is capable of taking in excess of 600 million readings in a single scan of 400 mm$^2$. It is desirable to reduce the amount of data passed on to the computer for final analysis in order that the analysis is speeded up and the amount of data required to be stored for archiving is reduced. This can be achieved by applying a threshold algorithm to the raw data. The invention makes use of two types of threshold algorithm. In "frequency table" thresholding each measurement is put into a table of intensity values. If a single measurement exceeds the average intensity of all the measurements taken to that point by a pre-set percentage (for example 20%) then that measurement is passed on to the computer. All measurements that do not exceed this threshold are discarded. In "dynamic thresholding" the system calculates a moving average of the signal and retains those measurements that are a pre-set percentage above the moving average. It is also possible to perform dynamic thresholding by continually measuring the slope of the signal response and triggering the start and finish of an event when the slope or rate of change of the slope is greater or lesser than a pre-set value or a set percentage of the average.

Frequency table thresholding works well when there are few bright objects in the sample and the background is low. Dynamic thresholding has the benefit that it can isolate and record the signals due to individual sites in the presence of significant concentrations of free label.

The raw data for one or more lines is retained for a short time by the system during scanning. This means that when an object such as a bead or cell is detected by thresholding, the measurement samples immediately before and after the object may be retained with the rest of the measurement samples for the object before rejection of the rest of the background data. These are termed pre- and post-samples.

FIG. 7 shows a typical scan map of fluorescent particles detected in a liquid sample by a Chemscan RDI instrument of the type shown in U.S. Pat. No. 5,663,059 while running a dynamic threshold. The left hand scan map displays all the fluorescent particles found; the right hand scan map displays those particles that match the characteristics determined for beads labelled with fluorescence in an assay performed by the method of the present embodiment.

Estimating the Size and Volume of the Bead or Cell

FIG. 8 gives the line amplitudes of a typical labelled bead. Beads and cells, being in many cases spherical, give line amplitude plots ("Z") that are "half sine wave" in X and Y. These plots are not exact replicas of the beads or cells. This is only an approximation. For example, the prototype has a beam energy that is Gaussian. A bead is spherical. Therefore, a correction for the true width of the bead is a combination of a Gaussian and a sine wave function. The sampling rate is higher than the scan rate so, for example, samples are taken every 1 $\mu$mm interval (scanning at 2 ms$^{-1}$ and sampling at 2 MHz), but the laser spot size is larger (6 $\mu$mm diameter). This means that the true diameter of a bead or cell will be approximately the width of the plot minus twice the diameter of the laser spot. Beads of known size are used to calibrate the instrument.

Measuring Bound and Free Fluorescence

If a bead or cell is smaller or equal to the laser spot diameter then the peak intensity on the line amplitude plot should be directly proportional to the amount of fluorophore bound to the bead or cell and the volume of fluorophore solution above it. This can be taken as the PVS. For beads or cells larger than the laser spot size the peak intensity value will under-read by an amount proportional to the diameter of the cell or bead which can be compensated for. The area under the 3-D plot can also be used to represent the PVS with an alternative calibration.

The UVS can be obtained from the pre- and -post samples taken before and after a bead or cell detected by a threshold algorithm.

In this way it is possible to obtain readings for both bound and free label without recording all the raw data collected. Correction can be made for the signal from free label that is added to the bound label by subtracting a corresponding portion of the UVS up to 100%. Alternatively, the dynamic threshold automatically provides a baseline for the free label contribution to the PVS and the bound label can be taken as the height or area of the peak above this threshold. It can be seen that a peak intensity value for the populated volume element can be obtained from the maxima on this plot, and that the intensity of the unpopulated volume element may be obtained from the pre-and post-samples at the edges of the plot.

The unpopulated volume element signal can also be obtained from the average background threshold recorded by the system or as the lowest signal obtained anywhere on the scan.

Statistical Sampling and Analysis

Individual beads or cells can vary enormously in key parameters such as size, number of binding sites or receptor expression. For these reasons it is unwise to rely on the measurement of signals from just a handful of beads or cells when collecting quantitative data. In the method of the invention a significant number of beads or cells may be used (typically 100–1000 in one sample). The key parameters such as peak or average intensities of all the beads or cells are recorded individually and this data is then processed as a population. Each bead or cell is effectively a separate assay and the data obtained for the population is typically a gaussian distribution (see FIG. 9).

The invention makes use of population statistics to provide accurate data for subsequent mathematical analysis. The values for peak intensity or area intensity of the target site and the adjacent free label intensity is recorded for every site in the sample. This data is plotted as a frequency histogram. A Gaussian fit is made to the population data and the mean value is returned. This same Gaussian fit method is applied to frequency histograms for other major discriminants such as size, shape and spectral characteristics. FIG. 10 shows a frequency histogram for the peak intensity of a bead population with intensity close to a background noise threshold cut-off. It can be seen that fitting these data to a Gaussian population gives an accurate representation of the population whereas an average would ignore results below the detectable threshold. FIG. 11 shows the correlation between histograms for different measurements of the same population. FIG. 12 shows a typical histogram for the "Gaussian shape" discriminant of a population of contaminating particles. Note that the population of contaminating particles is not itself Gaussian.

Correction for Effects of the Liquid Meniscus

The liquid meniscus can present problems when performing assays. It is desirable to have a fixed path-length through the liquid (uniform depth) to enable accurate and reproducible measurements both within a well and from one well to the next when scanning from above the sample. The meniscus also acts as a lens, potentially resulting in some of the sample being out of focus. Unfortunately, it can be extremely difficult to control the meniscus in the small volumes proposed for drug screening (<1 $\mu$l) with both a convex and concave meniscus possible in the same well. FIG. 6 illustrates the ability of the apparatus to plot the meniscus of a liquid sample. This sample was a droplet on a flat slide. The system has also been used to plot the menisci of samples in micro-wells, scanning from above or below. The free label concentration is substantially constant throughout the volume of the sample, thus the UVS can be used to plot the meniscus and a mathematical fit can be made to the data to correct for it's affect. The data can be greatly reduced by plotting the UVS from the signals obtained from sites detected by dynamic thresh-holding. This way, a thousand sites (e.g. cells) would provide several thousand UVS readings allowing the meniscus to be plotted sufficient for correction, albeit at lower resolution. The PVS/UVS ratio can be determined for every site by measuring peak intensity (for PVS) and average of pre- and post-samples (for UVS).

Calibration

The signal obtained from the detector is not always directly proportional to the laser diameter and liquid depth. For example:
1. The laser spot is focussed preferably on the bottom of the well. Depending on the optical set-up, the depth of focus may change with spot diameter. With the experimental system a laser spot size of 6 $\mu$m diameter gave a ±26 $\mu$m depth of focus. Increasing this to 10 $\mu$m gave a ±74 $\mu$m depth of focus. If the liquid depth is greater than the depth of focus, a portion of the laser volume element will be out of focus.
2. The light collection angle will be limited with light collection from molecules of label in the liquid closest to the detector being more efficient than those further away.
3. Refraction of emitted light at interfaces, particularly liquid/air, will reduce the efficiency of collection of light from molecules of label in the liquid.
4. Molecules in the path of the laser may attenuate the excitation or emission such that the signal obtained has a non-linear relationship to concentration for a given path length.
5. The detector may be non-linear over some of its range.

These problems can be corrected for by calibrating the system with beads of known fluorophore content and size dispersed in solutions of known depth and fluorophore concentration. The values obtained can be used in a software "look-up" table or can be used to derive algorithms to correct the basic mathematical model described in Example 1. Using these algorithms it is then possible to accurately estimate:

The depth of a fluid of known fluorophore concentration
The fluorophore concentration of a fluid of known depth The amount of fluorophore bound to or associated with an object within a fluorophore solution.

The laser spot is focussed on the bottom of the plate where the beads or cells are located. Magnetic beads may be used so that a magnet can pull the beads into the focal plane of the laser. Most of the solution itself is not within the depth of focus, but is illuminated by a cone of light. However, the pin hole of the detector has an area far greater than that of the spot size and the emission from this cone is collected. Thus we obtain a fluorescence signal that is similar to that which would be obtained had the beam been truly collimated. This gives a near-linear relationship between liquid depth and signal for any given low fluorophore concentration even beyond the depth of focus for the laser.

FIG. 13 shows a calibration of the apparatus with solutions of fluorescein of fixed depth and known concentration. FIG. 14 shows a calibration of the apparatus with beads of known fluorescein content (Sigma Chemical Co.) and size within a liquid of known depth.

Application of Discriminants

In example 2 the $K_d$ Of the ligand/receptor association is very low and the concentration of receptors on the site is relatively high. In this model experiment we would not expect significant interference from background contamination. In practical assays, particularly for drug discovery, it is common to have a weaker $K_d$ and lower concentration of receptors. A $K_d$ of $10^{-9}$ is typical with perhaps 50,000–100,000 receptors present on cells or a few 100,000 receptors on beads. It is also desirable to use low concentrations of labelled ligand to reduce cost or to avoid saturation of the receptors. This leads to lower signals from the assays. Naturally-occurring background auto-fluorescence from components of the assay, particularly cell culture components and particulates from the labelled ligand stock, can have brightness equal to or greater than the sites being assayed. Practical experiments have shown that in a real assay there may be as many as 60,000 contaminating objects in 1 $\mu$l with a brightness similar to that of the labelled site.

Purification of biological samples to reduce background contamination is expensive and often leads to reduced activity. It is desirable to be able to conduct assays with the minimum of component purification.

The present invention makes use of the line-to-line correlation, size discrimination, Gaussian shape criteria, colour discrimination and other discriminants described in U.S. Pat. No. 5,663,057 to reject the signals from contaminating objects. These discriminants were developed for positively identifying and counting bacteria which are labelled much brighter than the background and are thus not always adequate for rejecting background contamination in biochemical assays where the target analyte may be no brighter than the contamination. New discriminants have thus been added to the technique to perform the present invention:

Background noise close to the limit of sensitivity of the instrument can often show a Gaussian shape similar to the target in the primary channel. For low intensity signals the invention employs correlation between detectors. Target objects give signals that are Gaussian in more than one detector channel where background noise, such as electrical noise, does not.

Bacterial detection is aimed at rare event detection. The relative intensity of each event is not important provided it is above a threshold. The present invention requires an intensity value for both the bound and free label.

This example will illustrate how the method of the invention may be applied to estimate a dissociation constant for a bead-based assay and to measure the extent of competitive inhibition of this association by an active compound. FIG. 4 illustrates the measurement principles.

Magnetic beads coated with receptors are prepared. The number of receptors on the beads is estimated by incubating them in a solution of labelled ligand. The ligand concentration is chosen to be above the expected $K_d$ for the association. The amount of bound ligand is measured by drawing the beads to the focal point of the instrument with a magnet and scanning the suspension. A dynamic threshold algorithm is used to detect only those objects significantly brighter than the background. A set of discriminants for half-width, size, spectral ratios, Gaussian shape etc. are applied to the raw data and only those objects matching the characteristics of the beads are displayed.

The histograms for all the measurements on the beads are plotted and checked for Gaussian distribution in every parameter to confirm that the system has indeed discriminated beads from background contaminating particles. The signal due to the free ligand may be measured adjacent to the signal from the beads. Alternatively, the threshold algorithm may be set to zero the background and measure only peaks above this background. In this way the signal due to free label may be subtracted from the total signal to give only the signal on the beads.

The peak or average intensity of all the objects confirmed as beads is plotted in a frequency histogram. A Gaussian fit is made to this histogram and the intensity value at the centre of the distribution is taken as typical of the population. The number of molecules of fluorohore (and thus receptor) associated with the beads is then calculated by comparing the fluorescence value obtained with a calibration curve obtained for beads of known fluorophore content.

The $K_d$ of the association may be estimated by repeating the assay with a labelled ligand concentration below the expected $K_d$. A measure of the bound labelled ligand is obtained at equilibrium for the middle of the distribution of peak intensity values. The free ligand concentration at equilibrium is obtained from the signal from the solution adjacent to the beads. The volume of the beads may be estimated and a mathematical correction applied to the half-width measured for the beads.

The volume of the beads and the average number of receptor molecules per beads are now known. This can be represented as a local concentration.

The volume of free label illuminated by the laser and the concentration of that volume at equilibrium is now known.

A measure of the dissociation constant for the association can now be calculated by applying a mathematical model described below:

Simplified Mathematical Model

Referring to FIG. 4, the $K_d$ of a reversible receptor: ligand interaction can be estimated by assuming that the cell or bead represents a local concentration of receptor in which the receptor molecules are considered to be distributed evenly throughout the volume of the cell or bead. We will call this Bead Receptor concentration ($B_R$). This working assumption works well in practise for the bead and cell sizes and associated receptor numbers used in practical assays. Hence:

BV=Bead volume $N_{RB}$=Average number of receptors per bead $B_R = N_{RB}/(BV \times \text{Avogadro's No.})$ The free ligand concentration is assumed to be ligand concentration of the bulk liquid and to be substantially constant (no appreciable depletion of free ligand). To obtain an estimate of $K_d$ vs PVS/UVS we assume:

$N_{LB}$=predicted number of labelled ligand molecules on each bead (L)=bulk free ligand concentration IV=illumination volume of laser beam $N_{LB} = [L] \times N_{RB} \times BV \times \text{Avogadro's number}/(K_d + [L])$ Number of ligand molecules in UVS=$[L] \times IV \times$ Avogadro's number PVS=$\{(IV-BV) \times [L] \times \text{Avogrado's number}\} + N_{LB}$ Therefore, the model may predict $K_d$ vs PVS/UVS as plotted in FIG. 4. Once this plot is obtained the $K_d$ of an association may be estimated from a single measurement of the PVS/UVS signal obtained over a wide range of free ligand concentrations, and thus applied to multiple assays where the bound or free label is varying. This mathematical model showed good correlation with experimental results of PVS/UVS in example 3.

The technique allows for the estimation of $K_d$ by a single measurement without the need to test serial dilutions, however serial dilutions may be applied to improve the accuracy of the measurement. It is recognised that the $K_d$ for a receptor on a surface may vary from that in solution, however receptors are most often found on or in cell membranes. This technique provides a means of estimating $K_d$ for biomolecules in their natural environment.

The calculation can be reduced to a mathematical model embedded in software in the instrument. The instrument automatically determines the median peak intensity signals for the beads or cells, the number of beads or cells, their true dimensions and the signal due to free fluorescence. These values are applied to the mathematical model to directly calculate a measure of $K_d$ in real time. The instrument can also estimate the statistical confidence in the accuracy of the result.

Competitive inhibition by an active compound (for example, a candidate drug) can be measured from the change in bound: free signal ratios observed when the compound is added to a model assay. It is possible to estimate $IC_{50}$ in this way, and further to estimate the Kd of the compound.

Proof Measurements

A specific measured example, which we shall refer to as example 3, has been performed to confirm the theoretical assumptions made above, and this will now be described with reference to FIGS. 15 to 21.

In this example the reagents were goat anti-mouse antibody coated polystyrene microspheres, 5.5 µm diameter, binding capacity 1.48 µg mouse IgG/mg beads, $1.045 \times 10^8$ beads/ml in borate buffer (100 mM, pH8.5, containing 0.1% bovine serum albumin, 0.05% Tween, 10 mM EDTA and 0.1% sodium azide), stored at 4° C., supplied by Bang's Laboratories, Inc., 9025 Technology Drive, Fishers, Ind. 46038-2866, USA.

Mouse IgG, K (MOPC-21), fluorescein isothiocyanate (FITC) conjugate, immunoglobulin concentration 200 g/ml, protein concentration 200 g/ml, Fluorescein/protein molar ratio 5.8, in phosphate buffered saline (0.01 M, pH7.4, containing 1% bovine serum albumin and 15 mM sodium azide). Specificity (immunoelectrophoresis): single arc of precipitation versus anti-mouse whole serum, anti-mouse IgG1 and anti-mouse IgG K (prior to conjugation). Specificity (Ouchterlony Double Diffusion): single arc of precipitation with anti-mouse IgG1, no reaction with anti-mouse IgG2a, IgG2b, IgG3, IgM or IgA (prior to conjugation. Supplied by Sigma, 3050 Spruce Street, Saint Louis, Mo. 63103, USA.

Dubelcco's Phosphate Buffered Saline, (10 mM, pH7.4, containing 120 mM sodium chloride, without calcium or magnesium). Supplied by Life Technologies Ltd., P.O. Box 35, 3 Fountain Drive, Inchinnan Business Park Paisly, PA4 9RF, UK.

Quantum fluorescence beads at 450,000 molecules of equivalent soluble fluorochrome (450,000 MESF), 7–10 $\mu$m diameter, approximately $2 \times 10^6$ beads/ml in phosphate buffer containing surfactants and 0.1% sodium azide (information taken from product technical bulletin). Supplied by Sigma.

Fluorescein isothiocyanate (FITC) Isomer 1, approximately 98% pure (HPLC analysis). Supplied by Sigma.

The first requirement for the proof of the assay assumptions is to establish that the relationship between fluorescence and fluorophore concentration at a fixed pathlength and between fluorescence and pathlength for a fixed fluorophore concentration is linear.

The two biochemical parameters required in the proof are the $K_d$ of the binding interaction and the maximum number of available binding sites on a bead. These can both be measured in a single bead titration experiment.

The $K_d$ is the more obvious of the two measurements, being equivalent to the concentration of fluorescent ligand which results in half the maximum bead fluorescence, after the mean peak height bead intensity has been corrected for the intensity of the overlying ligand solution.

The maximum number of available sites on a bead can be found by plotting the aggregate fluorescence of the free ligand (the assay should be done under conditions that do not cause solution depletion) against ligand concentration at a fixed pathlength and PMT gain. After plotting fluorescence v ligand concentration, the concentration of ligand having solution fluorescence equal to that of the corrected mean peak bead intensity can be taken. This value and the pathlength value are input into appropriate calculation software and the effective number of fluorescent ligand molecules in the laser path is then calculated. The effective number of sites per bead is equal to this number. It is important that the response of solution fluorescence v pathlength is linear for this calculation.

It should be noted that although the laser light path will be conical, our model predicted that the effective number of fluorophore molecules within this cone can be calculated by assuming that the volume illuminated is that of a cylinder of diameter equal to the laser spot diameter.

It is important to correct the bead intensity value for the fluorescence of the overlying fluorophore solution because the beads used are translucent, allowing the laser light to excite any overlying fluorophore. The collection pinhole for the fluorescent light is 2 mm in diameter; therefore most of the solution fluorescence will not have to pass through the bead in order to be collected. This was proved experimentally by measuring the fluorescence of 450,000 MESF beads in different concentrations of fluorescein solution (in PBS; blank, 0.25 $\mu$M, 0.5 $\mu$M, and 1.0 $\mu$M) at a fixed depth (20 $\mu$m). A plot of uncorrected bead fluorescence v fluorescein concentration gave a straight line, when 100% of the solution fluorescence was subtracted, all the beads had a similar intensity (FIG. 17).

The ratio of mean corrected bead fluorescence to solution fluorescence can now be plotted against the bound to free reading predicted by software using the input values of $K_d$, available receptor sites, pathlength and fluorophore concentration. If the model is accurate and the $K_d$ and available receptor site values are correct, a graph of measured bound to free v predicted bound to free fluorescence should be a straight line with a slope of 1.

Experimental confirmation of the linear relationship between fluorescence and fluorophore concentration was achieved by measuring the fluorescence of several fluorescein solutions in Dubelcco's PBS at concentrations between 0.1 $\mu$M and 1 $\mu$M at a fixed photomultiplier gain and fixed pathlength (500 $\mu$m). The pathlength was fixed by inserting a purpose made plunging device, set to the required depth with vernier callipers, into the fluorescein solution. The solutions were scanned on the apparatus described above set to an aggregate fluorescence mode (thresholding effectively turned off to enable data collection from free solution), the fluorescence reading taken being the mean fluorescence estimated from the scan profile. A plot of fluorescence v fluorescein concentration gave a straight line (FIG. 15). Confirmation of the linear relationship between fluorescence and pathlength at the concentration employed at fixed PMT gain was achieved in a similar manner, using a 1 $\mu$M solution of fluorescein and varying the depth of the plunger device, set using vernier callipers. A plot of fluorescence v pathlength gave a straight line (FIG. 16).

Solutions of MOPC-21-FITC conjugate at concentrations of 1 nM, 5 nM, 10 nM, 50 nM, 100 nM, 500 nM 1.0 $\mu$M and were prepared in Dubelcco's PBS. Goat anti-mouse beads were re-suspended by vortex mixing and were diluted to a concentration of 2,500 beads/$\mu$l with Dubelcco's PBS. This diluted bead suspension was then added to each of the MOPC-21-FITC solutions (2 $\mu$l beads plus 100 $\mu$l solution to give a final concentration of 50 beads/$\mu$l), a PBS buffer blank was included. After mixing, the reaction tubes were incubated for 3 hours in the dark, at room temperature and mixed occasionally.

The bead suspensions (50 $\mu$l of each) were then scanned from below in a clear-bottom microtitre plate in the apparatus described above, with sample depth fixed at 200 $\mu$m.

The threshold algorithms were set to pick out each individual bead, and data was collected for peak intensity and half width. The solution flourescence value (UVS) was obtained by switching off the threshold and scanning a coarser profile. The solution fluorescence value was taken as the midline of the scan profile displayed. The uncorrected bead mean peak height fluorescence intensity (PVS) for each solution concentration was taken from the scan results screen, together with the standard deviation value and the number of results seen. In order to isolate the signal due to the bead only, the solution fluorescence was subtracted from the mean bead peak intensity fluorescence value for each data point. The corrected bead fluorescence was then plotted against MOPC-21-FITC concentration (FIG. 18). From this plot it was apparent that a secondary ligand binding was beginning to occur above ligand concentrations of 100 nM (FIG. 18), possibly antibody-antibody self-binding. It was therefore decided to plot the titration curve to 100 nM (FIG. 19) and estimate the $K_d$ of the interaction and the number of available receptors per bead from this graph, as described above, after plotting solution fluorescence v MOPC-21-FITC concentration (FIG. 20). The experimental bound to free results were plotted against the predicted values (FIG. 21).

The $K_d$ of the binding interaction was found to be 1.2 nmoles/l and the maximum number of available binding sites/bead was found to be 245,000. The plot of experimental bound to free ratio against predicted PVS/UVS ratio was linear with a slope of 1.86. The linearity is more important than the slope in this proof since it has been assumed that the laser spot size is 6 µm, any variation in this value will affect the predicted B/F values in a linear fashion.

This example proves that the apparatus of the invention may be used to measure and estimate the Kd of an association; the size and volume of a bead or cell; the number of binding sites on the bead or cell; the free label concentration and the occupancy of the binding sites during an assay. Furthermore, once calibrated the system and method of the invention may be used to estimate the KD of a reversible binding interaction in a single well without the need for serial dilutions or separation by employing a simple mathematical model to the measurements obtained.

This fundamental principle can be applied to the measurement of more complex interactions involving multiple dissociation constants, and can also be used to estimate the KD of a competing compound.

What is claimed is:

1. A method of performing a non-separation assay for determining a level of binding of one component to another, the method comprising:
    providing a first labelled component in a solution;
    providing an array of beads, cells, surfaces or wells and placing a second component onto said beads or surfaces or into said cells or wells;
    immersing the array with the solution;
    scanning the array with an illuminating light beam such that the light passes through the solution whilst illuminating the beads, cells, surfaces or wells;
    determining an intensity of light received from each of the beads, cells, surfaces or wells and solution at at least one wavelength during illumination;
    determining from a peak intensity value of light received, an area beneath a plot of the peak intensity, or the area beneath a 3-D intensity plot of a second component location, an amount of binding of the first labelled component to the second component;
    determining from pre- and post-second component intensity values, the lowest intensity signal obtained during the scan of the array or an average background value obtained during the scan, an amount of first labelled component in the solution; and
    determining a ratio of i) an amount of binding of the first labelled component to the second component to ii) the amount of first labelled component in the solution.

2. A method of claim 1, wherein the illuminating light is generated by a laser beam.

3. A method according to claim 1, wherein the received light is a light generated by a fluorescence.

4. A method according to claim 1, wherein more than one wavelength of light is received.

5. A method according to claim 1, wherein the received intensity is employed to determine i) at least one of a diameter and a volume of each bead, cell, or well or ii) a diameter of a surface, and a number of molecules bound to the bead, cell, surface or well.

6. A method according to claim 1, wherein the illuminating light is arranged to illuminate from above or below a sample with an emitted light being detected from above or below the sample in any combination in such a way that the illuminating light illuminates both the bead, cell, surface or well and a significant volume of the solution above or adjacent to the bead, cell surface or well.

7. A method according to claim 1, wherein the illuminating light beam scans the solution and beads, cells, surfaces or wells in a linear fashion, with one scan overlapping the next, so that a continuous measurement of received light intensity can be provided.

8. A method according to claim 1, wherein data relating to the received light intensity is filtered by employment of a fixed or variable threshold in order to reduce an amount of data required to be processed.

9. A method according to claim 1, further comprising using a threshold to isolate beads, cells, surfaces or wells having associated binding sites from a background free label signal in such a way that pre- and post-threshold signal samples can be used as a measure of free label adjacent to each bead, cell, surface or well, and correcting for effects of a liquid meniscus.

10. A method according to claim 9, wherein a fingerprint or discriminants are used to pick out a population of beads, cells, surfaces or wells having associated binding sites from background contaminating particles before determining the amount of binding and the amount of first labelled component in the solution associated with the binding sites.

11. An apparatus for performing a non-separation assay for determining a level of binding of a first labelled component in solution to a second component on an array of sites, the apparatus comprising:
    scanning means for scanning the array with an illuminating light beam such that the light passes through the solution whilst illuminating beads, cells, surfaces or wells;
    means for determining an intensity of light received from each of the beads, cells, surfaces or wells and solution at at least one wavelength during illumination;
    means for receiving light intensity; and
    means for determining from a peak intensity value of light received, an area beneath a plot of the peak intensity, or the area beneath a 3-D intensity plot of a second component location, an amount of binding of the first labelled component to the second component;
    means for determining from pre- and post-second component intensity values, the lowest intensity signal obtained during the scan of the array or an average background value obtained during the scan, an amount of first labelled component in the solution; and
    means for determining a ratio of i) an amount of binding of the first labelled component to the second component to ii) the amount of first labelled component in the solution.

12. An apparatus of claim 11, wherein the scanning means includes a laser beam.

13. An apparatus according to claim 11, wherein more than one wavelength of light is received.

14. An apparatus according to claim 11, wherein the determining means employs the received intensity to determine i) at least one of a diameter and a volume of each bead, cell, or well or ii) a diameter of a surface, and a number of molecules bound to the bead, cell, surface or well.

15. An apparatus according to claim 11, wherein the illuminating light is arranged to illuminate from above or below a sample with an emitted light being detected from above or below the sample in any combination in such a way that the illuminating light illuminates both the bead, cell, surface or well and a significant volume of the solution above or adjacent to the bead, cell, surface or well.

16. An apparatus according to claim 11, wherein the illuminating light beam scans the solution and beads, cells, surfaces or wells in a linear fashion, with one scan overlapping the next, so that a continuous measurement of received light intensity can be provided.

17. An apparatus according to claim 11, wherein data relating to the received light intensity is filtered by the employment of a fixed or variable threshold in order to reduce an amount of data required to be processed.

18. An apparatus according to claim 11, further comprising means for collecting the received light.

19. An apparatus according to claim 18, wherein the means for collecting the received light includes a pin hole.

20. A method according to claim 10, wherein a Gaussian fit is made to the population, and a mean value thereof is utilized to determine the amount of binding and amount of first labelled component in the solution.

21. A method according to claim 1, wherein compensation of the amount of binding, for an effect of first labelled component in solution around a bead, cell, surface or well, is provided by subtracting the received intensity of first labelled component in solution from the received intensity of first labelled component bound to that bead, cell, surface or well.

22. A method according to claim 2, wherein the array is an array of beads and a bead in the array is a magnetic bead, and a magnet is provided such that the magnet pulls the bead into a focal plane.

23. An apparatus according to claim 11, further comprising means for compensating the determined amount of binding, for an effect of first labelled component in solution around a bead, cell, surface or well, by subtracting the received intensity of first labelled component in solution from the received intensity of first labelled component bound to that bead, cell, surface or well.

24. An apparatus according to claim 12, wherein the array of is an array of beads and a bead in the array is a magnetic bead, and a magnet is provided such that it pulls the bead into the focal plane of the laser beam.

25. A method according to claim 1, wherein a number of beads or cells in the array is determined.

26. An apparatus according to claim 11, further comprising means for determining a number of beads or cells in the array.

27. A method according to claim 1, wherein the dissociation constant (Kd) of the binding is determined from the ratio of the amount of binding to the amount of first labelled component in the solution.

28. An apparatus according to claim 11, further comprising means for determining, from the ratio of the amount of binding to the amount of first labelled component in solution, a dissociation constant of the binding.

29. A method according to claim 1, wherein data relating to the received light intensity is filtered by employment of a fixed or variable threshold in order to detect one or more beads, cells, surfaces or well.

30. An apparatus according to claim 11, wherein data relating to the received light intensity is filtered by employment of a fixed or variable threshold in order to detect one or more beads, cells, surfaces or well.

31. A method according to claim 1, wherein competitive inhibition by an active compound added to the assay is determined from a change in the ratio of i) the amount of binding of the first labelled component to the second component to ii) the amount of first labelled component in the solution when the compound is added.

32. A method according to claim 31, wherein a dissociation constant of the active compound added to the assay is determined from the determined competitive inhibition.

33. An apparatus according to claim 11, wherein competitive inhibition by an active compound added to the assay is determined from a change in the ratio of i) the amount of binding of the first labelled component to the second component to ii) the amount of first labelled component in the solution when the compound is added.

34. An apparatus according to claim 33, wherein a dissociation constant of the active compound added to the assay is determined from the determined competitive inhibition.

* * * * *